US011191825B2

United States Patent
Martinez

(10) Patent No.: US 11,191,825 B2
(45) Date of Patent: Dec. 7, 2021

(54) COMPOSITIONS AND METHODS FOR VACCINATION AGAINST INFLUENZA

(71) Applicant: VACCITECH, INC., Rowland Heights, CA (US)

(72) Inventor: Luis Mario Rodriguez Martinez, Torreon (MX)

(73) Assignee: Vaccitech, Inc., Rowland Heights, CA (US)

(*) Notice: Subject to any disclaimer, the term of this patent is extended or adjusted under 35 U.S.C. 154(b) by 0 days.

(21) Appl. No.: 16/332,245

(22) PCT Filed: Sep. 14, 2017

(86) PCT No.: PCT/US2017/051633
§ 371 (c)(1),
(2) Date: Mar. 11, 2019

(87) PCT Pub. No.: WO2018/053178
PCT Pub. Date: Mar. 22, 2018

(65) Prior Publication Data
US 2019/0307877 A1    Oct. 10, 2019

Related U.S. Application Data

(60) Provisional application No. 62/396,041, filed on Sep. 16, 2016.

(51) Int. Cl.
| | | |
|---|---|---|
| *A61K 39/145* | (2006.01) | |
| *A61P 31/16* | (2006.01) | |
| *C07K 14/11* | (2006.01) | |
| *C07K 14/005* | (2006.01) | |
| *A61P 37/04* | (2006.01) | |
| *A61K 39/12* | (2006.01) | |
| *A61K 39/00* | (2006.01) | |

(52) U.S. Cl.
CPC .......... *A61K 39/145* (2013.01); *A61K 39/12* (2013.01); *A61P 31/16* (2018.01); *A61P 37/04* (2018.01); *C07K 14/11* (2013.01); *A61K 2039/53* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

2010/0310604 A1* 12/2010 D'Aoust ........ C12Y 503/04001
424/210.1
2012/0301504 A1* 11/2012 Khurana .............. A61K 39/145
424/210.1

FOREIGN PATENT DOCUMENTS

MX    2011013020    12/2011

OTHER PUBLICATIONS

GenBank Accession# KM821347, Influenza A virus (A/Victoria/361/2011(H3N2)) segment 4 hemagglutinin (HA) gene, complete cds., 2014.*
GenBank Accession# AIU46088, hemagglutinin [Influenza A virus (A/Victoria/361/2011(H3N2))]., 2014.*
Alan R. Davis, Expression of antigenic determinants of the hemagglutinin gene of a human influenza virus in *Escherichia coli*, Proceedings of the National Academy of Sciences of the United States of America, Sep. 1981, pp. 5376-5380, vol. 78, No. 9, United States National Academy of Sciences.
Zuzana Biesova, Preparation, characterization, and immunogenicity in mice of a recombinant influenza H5 hemagglutinin vaccine against the avian H5N1 A/Vietnam/1203/2004 influenza virus, Vaccine, Oct. 2009, pp. 6234-6238. 27(44), Elsevier.
Jose M. Aguilar, An Influenza A/H1N1/2009 Hemagglutinin Vaccine Produced in *Escherichia coli*, Plos One, Jul. 2010, vol. 5, Issue 7, e11694.
Manabu Igrashi, Predicting the Antigenic Structure of the Pandemic (H1N1) 2009 Influenza Virus Hemagglutinin, Plos One, Jan. 2010, vol. 5, Issue 7, e8553.
Langzhou Song, Efficacious Recombinant Influenza Vaccines Produced by High Yield BActerial Expression: A Solution to Global Pandemic and Seasonal Needs, Plos One, May 2008, vol. 3, Issue 5, e2257.
Luis Mario Rodriguez Martinez, Engineering the production of viral antigens and recombinant antiviral proteins: Opportunistic response to pandemic events, School of Engineering and Sciences, Nov. 2016, Instituto Tecnológico y de Estudios Superiores de Monterrey, Monterrey Nuevo León México.
Francesco Berlanda Scorza, Universal influenza vaccines: Shifting to better vaccines, Vaccine, Mar. 2016, pp. 2926-2933, 34, Elsevier.
Tanya Gottlieb, Epitope-based approaches to a universal influenza vaccine, Journal of Autoimmunity, Aug. 2014, pp. 15-20, 54, Elsevier.
Bo Wen, Signal peptide replacements enhance expression and secretion of hepatitis C virus envelope glycoproteins, Acta Biochim Biophys Sin, 2011, pp. 96-102, vol. 43, Issue 2, ABBS Editorial Office.
Patent Cooperation Treaty, International Search Report.

* cited by examiner

*Primary Examiner* — Benjamin P Blumel
(74) *Attorney, Agent, or Firm* — Kevin Schraven; Anooj Patel; Hankin Patent Law, APC

(57) ABSTRACT

Described herein are methods and compositions for vaccination against influenza. The compositions comprise recombinant engineered influenza hemagglutinin polypeptides. Also disclosed are methods of producing recombinant engineered influenza hemagglutinin polypeptides in cell-based systems.

13 Claims, 6 Drawing Sheets
Specification includes a Sequence Listing.

(I) Molecular Engineering — 1

(II) Cell Engineering — 2

(III) Bioprocess Engineering — 3

Recombinant Influenza Antigen — 4

Figure 1

COMPOSITIONS AND METHODS FOR VACCINATION AGAINST INFLUENZA

CROSS REFERENCE TO RELATED APPLICATIONS

This application is a U.S. National Phase of International Application No. PCT/US2017/051633 filed Sep. 14, 2017, which claims the benefit of U.S. Provisional Application Ser. No. 62/396,041 filed on Sep. 16, 2016 which is incorporated by reference in its entirety.

SEQUENCE LISTING

The instant application contains a Sequence Listing which has been submitted electronically in ASCII format and is hereby incorporated by reference in its entirety. Said ASCII copy, created on Jun. 11, 2019 is named 49612-701_831_SL and is 43,094 bytes in size.

BACKGROUND OF THE INVENTION

In the United States approximately 36,000 people die, and 200,000 people are hospitalized annually due to influenza and its complications. Influenza disproportionately affects the elderly, the young, those who are immunocompromised, and pregnant women. Currently prophylactic treatment via vaccination is the best way to prevent flu related death, disease and epidemic spread to at-risk individuals. However, influenza presents a significant challenge to vaccination efforts. Since the influenza virus is seasonal, and possesses a high mutation rate, a new vaccine must be reformulated every year with the correct influenza strains.

Influenza is an RNA virus of the family Orthomyxoviridae. This family comprises five different genera, of which, three are influenza viruses; A, B, and C. All three genera are capable of infecting humans, but most disease is caused by type A, and to a lesser degree by types B and C. Type A can be further subdivided into serotypes (subtypes) based upon the differing antibody responses to their surface proteins; hemagglutinin and neuraminidase (sialidase). The serotype is usually designated using an "H" number that designates a particular hemagglutinin, and an "N" number that designates a particular neuraminidase. The two most common human disease causing serotypes are H1N1, which caused the 1918 Spanish flu epidemic, and H3N2. Different influenza strains of either serotype are named using the genera, geographical location, sample number, and year of isolation. For example, A/Moscow/10/1999.

The seasonal flu vaccine, in general, contains 3 or 4 different strains chosen before the start of the flu season. The traditional flu vaccine comprises inactivated whole-virus produced in chicken eggs, and is delivered by intradermal injection. There is a vaccine available that contains live attenuated virus, also grown in chicken eggs, that is delivered in the form of an intranasal mist (FluMist®). Additionally, there is currently a single vaccine on the market made without the use of eggs, (Flublok®). This vaccine uses a baculovirus expression system in insect cells for production, and comprises the entire hemagglutinin protein.

Traditional vaccines grown in eggs present several problems. Production of the seasonal vaccine occurs on a tight time schedule only allowing a few months for production after that season's strains have been selected. The selected strains may not grow well, or grow slowly, leading to delays in delivery of the vaccine for the start of flu season. Batches can be easily contaminated leading to further delays or reduced supply. The product can be heterogeneous due to the inherent ability of live grown flu virus to mutate and recombine. Additionally, virus grown in eggs can present a hazard to those with egg allergies. A recombinant vaccine on the other hand would allow for a safer more homogenous product, that is delivered more quickly and at lower cost.

SUMMARY OF THE INVENTION

In certain embodiments, described herein, is a composition comprising one or more isolated, engineered influenza polypeptides, wherein the one or more isolated, engineered influenza polypeptides: (a) comprise a hemagglutinin $HA_1$ domain, and (b) do not comprise a hemagglutinin $HA_2$ domain or a transmembrane domain. In certain embodiments, the composition comprises two or more isolated, engineered influenza polypeptides. In certain embodiments, the composition comprises three or more isolated, engineered influenza polypeptides. In certain embodiments, the composition comprises four or more isolated, engineered influenza polypeptides. In certain embodiments, the composition comprises five or more isolated, engineered influenza polypeptides. In certain embodiments, any of the one or more isolated, engineered influenza polypeptides comprises a signal sequence that directs secretion of the polypeptide from a cell. In certain embodiments, any of the one or more isolated, engineered influenza polypeptides is from an influenza type A or B. In certain embodiments, any of the one or more isolated, engineered influenza polypeptides is from an influenza type B. In certain embodiments, any of the one or more isolated, engineered influenza polypeptides is from an influenza type A. In certain embodiments, any of the one or more isolated, engineered influenza polypeptides is from an H1N1 or H3N2 subtype. In certain embodiments, the $HA_1$ domain of any of the one or more isolated, engineered influenza polypeptides is greater than 10 amino acids in length. In certain embodiments, the $HA_1$ domain of any of the one or more isolated, engineered influenza polypeptides is greater than 40 amino acids in length. In certain embodiments, the $HA_1$ domain of any of the one or more isolated, engineered influenza polypeptides is less than 300 amino acids in length. In certain embodiments, any of the one or more isolated, engineered influenza polypeptide is from the naturally occurring influenza strains selected from the group consisting of A/Moscow/10/1999, A/New Caledonia/20/1999, B/Sichuan/379/99, A/Panama/2007/1999, B/Hong Kong/330/2001, A/Wyoming/03/2003, B/Shanghai/361/2002, A/Wisconsin/67/2005, B/Malaysia/2506/2004, A/Hiroshima/52/2005, B/Ohio/1/2005, A/Solomon Islands/3/2006, A/Brisbane/59/2007, A/Brisbane/10/2007, B/Florida/4/2006, B/Brisbane/60/2008, A/California/7/2009, A/Perth/16/2009, A/Victoria/361/2011, B/Massachusetts/02/2012, and combinations thereof. In certain embodiments, any of the one or more isolated, engineered influenza polypeptides comprises an amino acid sequence with at least 95% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more isolated, engineered influenza polypeptides comprises an amino acid sequence with at least 99% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:

9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more isolated, engineered influenza polypeptides comprises an amino acid sequence with 100% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more isolated, engineered influenza polypeptides further comprises an enterokinase cleavage sequence (Asp-Asp-Asp-Asp-Lys). In certain embodiments, any of the one or more isolated, engineered influenza polypeptides was produced in yeast. In certain embodiments, the yeast is *Pichia pastoris*. In certain embodiments, the yeast has been modified to produce a polypeptide glycosylation pattern characteristic of a human. In certain embodiments, any of the one or more engineered influenza polypeptides is encoded by a polynucleotide. In certain embodiments, the nucleotide sequence is codon optimized for expression in yeast. In certain embodiments, the polynucleotide further comprises a yeast promoter region 5 prime to the nucleotide sequence encoding any of the engineered influenza polypeptides. In certain embodiments, the composition further comprises a pharmaceutically acceptable excipient. In certain embodiments, the composition further comprises an immunological adjuvant.

In certain embodiments, described herein, is a method of manufacturing an influenza vaccine comprising manufacturing one or more isolated, engineered influenza polypeptides, wherein the polypeptide is synthesized, in vitro translated or produced in a cellular expression system, wherein the one or more isolated, engineered influenza polypeptides: (a) comprises a hemagglutinin $HA_1$ domain, and (b) do not comprise a hemagglutinin $HA_2$ or transmembrane domain. In certain embodiments, the method comprises manufacturing two or more isolated, engineered influenza polypeptides. In certain embodiments, the method comprises manufacturing three or more isolated, engineered influenza polypeptides. In certain embodiments, the method comprises manufacturing four or more isolated, engineered influenza polypeptides. In certain embodiments, the method comprises manufacturing five or more isolated, engineered influenza polypeptides. In certain embodiments, any of the one or more isolated, engineered influenza polypeptides comprises a signal sequence that directs secretion of the polypeptide from a cell. In certain embodiments, any of the one or more isolated, engineered influenza polypeptides is from an influenza type A or B. In certain embodiments, any of the one or more isolated, engineered influenza polypeptides is from an influenza type B. In certain embodiments, any of the one or more isolated, engineered influenza polypeptides is from an influenza type A. In certain embodiments, any of the one or more isolated, engineered influenza polypeptides is from an H1N1 or H3N2 subtype. In certain embodiments, the $HA_1$ domain of any of the one or more isolated, engineered influenza polypeptides is greater than 10 amino acids in length. In certain embodiments, the $HA_1$ domain of any of the one or more isolated, engineered influenza polypeptides is greater than 40 amino acids in length. In certain embodiments, the $HA_1$ domain of any of the one or more isolated, engineered influenza polypeptides is less than 300 amino acids in length. In certain embodiments, any of the one or more isolated, engineered influenza polypeptides is immunogenic in a human subject. In certain embodiments, the polypeptide sequence of the $HA_1$ domain is selected from the group comprising the influenza strains A/Moscow/10/1999, A/New Caledonia/20/1999, B/Sichuan/379/99, A/Panama/2007/1999, B/Hong Kong/330/2001, A/Wyoming/03/2003, B/Shanghai/361/2002, A/Wisconsin/67/2005, B/Malaysia/2506/2004, A/Hiroshima/52/2005, B/Ohio/1/2005, A/Solomon Islands/3/2006, A/Brisbane/59/2007, A/Brisbane/10/2007, B/Florida/4/2006, B/Brisbane/60/2008, A/California/7/2009, A/Perth/16/2009, A/Victoria/361/2011, B/Massachusetts/02/2012, and combinations thereof. In certain embodiments, any of the one or more isolated, engineered influenza polypeptides comprises an amino acid sequence with at least 95% amino acid sequence similarity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more isolated, engineered influenza polypeptides comprises an amino acid sequence with at least 99% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more isolated, engineered influenza polypeptides comprises an amino acid sequence with 100% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more isolated, engineered influenza polypeptides further comprises the remnant of a cleaved fusion tag cleavage site. In certain embodiments, any of the one or more isolated, engineered influenza polypeptides was produced in yeast. In certain embodiments, the yeast is *Pichia pastoris*. In certain embodiments, the yeast has been modified to produce a polypeptide glycosylation pattern characteristic of a human. In certain embodiments, the method further comprises admixing any of the one or more isolated, engineered influenza polypeptides with a pharmaceutically acceptable excipient. In certain embodiments, admixing any of the one or more isolated, engineered influenza polypeptides with an immunological adjuvant.

In certain embodiments, described herein, is a method for immunizing a subject against influenza comprising administering a composition comprising one or more isolated, engineered influenza polypeptides, wherein the one or more isolated, engineered influenza polypeptides: (a) comprise a hemagglutinin $HA_1$ domain, and (b) do not comprise a hemagglutinin $HA_2$ domain or a transmembrane domain. In certain embodiments, the composition comprises two or more isolated, engineered influenza polypeptides. In certain embodiments, the composition comprises three or more isolated, engineered influenza polypeptides. In certain embodiments, the composition comprises four or more isolated, engineered influenza polypeptides. In certain embodiments, the composition comprises five or more isolated, engineered influenza polypeptides. In certain embodiments, any of the one or more isolated, engineered influenza polypeptides comprises a signal sequence that directs secretion of the polypeptide from a cell. In certain embodiments, any of the one or more isolated, engineered influenza polypeptides is from an influenza type A or B. In certain embodiments, any of the one or more isolated, engineered influenza polypeptides is from an influenza type B. In certain embodiments, any of the one or more isolated, engineered influenza polypeptides is from an influenza type A. In certain embodiments, any of the one or more isolated, engineered influenza polypeptides is from an H1N1 or H3N2 subtype. In certain embodiments, the $HA_1$ domain of any of the one or more isolated, engineered influenza polypeptides is greater than 10 amino acids in length. In certain embodiments, the $HA_1$ domain of any of the one or more isolated, engineered influenza polypeptides is greater than 40 amino acids in length. In certain embodiments, the $HA_1$ domain of any of the one or more isolated, engineered influenza polypeptides is less than 250 amino acids in length. In certain embodiments, any of the one or more isolated, engineered influenza polypeptides is immunogenic in a human subject. In certain embodiments, the polypeptide sequence of the $HA_1$ domain is selected from the group comprising the influenza strains A/Moscow/10/1999, A/New_Caledonia/20/1999, B/Sichuan/379/99, A/Panama/2007/1999, B/Hong_Kong/330/2001, A/Wyoming/03/2003, B/Shanghai/361/2002, A/Wisconsin/67/2005, B/Malaysia/2506/2004, A/Hiroshima/52/2005, B/Ohio/1/2005, A/Solomon Islands/3/2006, A/Brisbane/59/2007, A/Brisbane/10/2007, B/Florida/4/2006, B/Brisbane/60/2008, A/California/7/2009, A/Perth/16/2009, A/Victoria/361/2011, B/Massachusetts/02/2012, and combinations thereof. In certain embodiments, any of the one or more isolated, engineered influenza polypeptides comprises an amino acid sequence with at least 95% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more isolated, engineered influenza polypeptides comprises an amino acid sequence with at least 99% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more isolated, engineered influenza polypeptides comprises an amino acid sequence with 100% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, In certain embodiments, any of the one or more isolated, engineered influenza polypeptides further comprises the remnant of a cleaved fusion tag cleavage site. In certain embodiments, any of the one or more isolated, engineered influenza polypeptides was produced in yeast. In certain embodiments, the yeast is *Pichia pastoris*. In certain embodiments, the yeast has been modified to produce a polypeptide glycosylation pattern characteristic of a human. In certain embodiments, the composition further comprises administering a pharmaceutically acceptable excipient. In certain embodiments, the composition further comprises administering an immunological adjuvant. In certain embodiments, the subject is a human.

In certain embodiments, described herein, is a method for determining a subject's response to immunization with an influenza vaccine the method comprising: obtaining a biological sample from a subject that has been administered a composition comprising any one or more isolated, engineered influenza polypeptides comprising an amino acid sequence with at least 95% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof; and detecting an interaction between an antibody from the subject and any of the one or more isolated, engineered influenza polypeptides comprising an amino acid sequence with at least 95% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, the subject is a human subject. In certain embodiments, the biological sample comprises blood, plasma, or serum. In certain embodiments, detecting an interaction between an antibody from the subject and any of the one or more isolated, engineered influenza polypeptides comprising an amino acid sequence with at least 95% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof, comprises performing an enzyme-linked immunosorbent assay (ELISA) or a homogenous immunoassay. In certain embodiments, the method further comprises determining an antibody titer specific for any of the one or more isolated, engineered influenza polypeptides comprising an amino acid sequence with at least 95% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof.

In certain embodiments, described herein, is a method of producing an influenza vaccine comprising: expressing one or more engineered influenza polypeptides in a cellular expression system, wherein the one or more engineered influenza polypeptides: (a) comprise a hemagglutinin $HA_1$ domain, and (b) do not comprise a hemagglutinin $HA_2$ domain or a transmembrane domain. In certain embodiments, the method further comprises isolating the expressed one or more engineered influenza polypeptides. In certain embodiments, the cellular expression system comprises yeast cells. In certain embodiments, the yeast cells are

*Pichia pastoris*. In certain embodiments, the *Pichia pastoris* yeast cells are strain GS115. In certain embodiments, the yeast has been modified to produce a polypeptide glycosylation pattern characteristic of a human. In certain embodiments, any of the one or more engineered influenza polypeptides comprises an amino acid sequence with at least 95% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more engineered influenza polypeptides comprises an amino acid sequence with at least 99% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more engineered influenza polypeptides comprises an amino acid sequence with 100% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, the one or more engineered influenza polypeptides is expressed from a nucleic acid encoding the one or more engineered influenza polypeptides. In certain embodiments, the nucleic acid is integrated into the genome of the cellular expression system. In certain embodiments, the method further comprises admixing any of the one or more expressed engineered influenza polypeptides with a pharmaceutically acceptable excipient. In certain embodiments, the method further comprises admixing any of the one or more expressed engineered influenza polypeptides with an immunological adjuvant.

In certain embodiments, described herein, is an expression construct comprising: a first polynucleotide encoding a signal sequence that directs secretion of the polypeptide from a cell; a second polynucleotide encoding one or more engineered influenza polypeptides, wherein the one or more engineered influenza polypeptides: (a) comprise a hemagglutinin $HA_1$ domain, and (b) do not comprise a hemagglutinin $HA_2$ domain or a transmembrane domain; a third polynucleotide encoding a cleavage site; and a fourth polynucleotide encoding a tag for purification, wherein second polynucleotide is codon optimized for expression in yeast. In certain embodiments, all of the first, second, third, or fourth polynucleotides are codon optimized for expression in yeast. In certain embodiments, any of the one or more engineered influenza polypeptides is from an influenza type A or B. In certain embodiments, any of the one or more engineered influenza polypeptides is from an influenza type B. In certain embodiments, any of the one or more engineered influenza polypeptides is from an influenza type A. In certain embodiments, any of the one or more engineered influenza polypeptides is from an H1N1 or H3N2 subtype. In certain embodiments, the $HA_1$ domain of any of the one or more engineered influenza polypeptides is greater than 10 amino acids in length. In certain embodiments, the $HA_1$ domain of any of the one or more engineered influenza polypeptides is greater than 40 amino acids in length. In certain embodiments, the $HA_1$ domain of any of the one or more engineered influenza polypeptides is less than 300 amino acids in length. In certain embodiments, any of the one or more engineered influenza polypeptides is immunogenic in a human. In certain embodiments, the polypeptide sequence of the $HA_1$ domain is selected from the group comprising the influenza strains A/Moscow/10/1999, A/New_Caledonia/20/1999, B/Sichuan/379/99, A/Panama/2007/1999, B/Hong_Kong/330/2001, A/Wyoming/03/2003, B/Shanghai/361/2002, A/Wisconsin/67/2005, B/Malaysia/2506/2004, A/Hiroshima/52/2005, B/Ohio/1/2005, A/Solomon Islands/3/2006, A/Brisbane/59/2007, A/Brisbane/10/2007, B/Florida/4/2006, B/Brisbane/60/2008, A/California/7/2009, A/Perth/16/2009, A/Victoria/361/2011, B/Massachusetts/02/2012, and combinations thereof. In certain embodiments, any of the one or more engineered influenza polypeptides comprises an amino acid sequence with at least 95% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more engineered influenza polypeptides comprises an amino acid sequence with at least 99% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, any of the one or more engineered influenza polypeptides comprises an amino acid sequence with 100% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In certain embodiments, the expression construct is a polynucleotide and is maintained in a yeast cell. In certain embodiments, the yeast is *Pichia pastoris*. In certain embodiments, the yeast has been modified to produce a polypeptide glycosylation pattern characteristic of a human. In certain embodiments, the expression construct is integrated into the genome. In certain embodiments, the yeast is stored in a master cell bank comprising a plurality of yeast cells as described herein, wherein the master cell bank comprises yeast cells admixed with a cryopreservative. In certain embodiments, the cryopreservative is glycerol.

BRIEF DESCRIPTION OF THE DRAWINGS

FIG. 1 depicts a schematic of the production of an isolated, engineered influenza polypeptide.

DETAILED DESCRIPTION OF THE INVENTION

Certain Definitions

Figure 2:
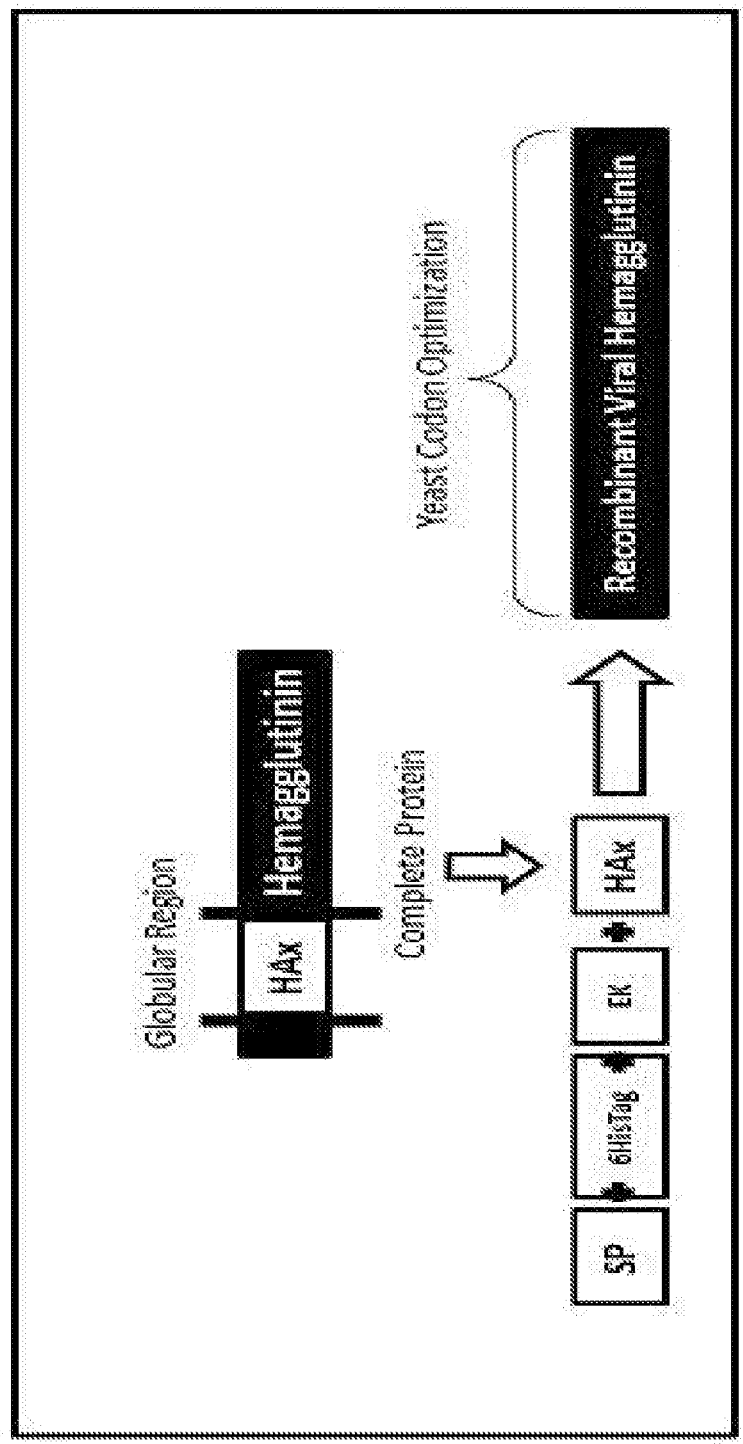
FIG. 2 depicts a schematic illustration of a non-limiting embodiment of an engineered hemagglutinin polypeptide of this disclosure.

As used herein "isolated" is synonymous with "purified" and means that a polypeptide that is produced in a cell-based production system is subjected to one or more steps that remove impurities such as non-influenza proteins and polypeptides; cell membrane or cell wall components; and factors secreted from a cell-based system that are not influenza polypeptides; such as carbohydrates, lipids, peptides, or other small molecules. Steps that remove impurities include, but are not limited to, organic extraction, precipitation, concentration, filtration, ultrafiltration, tangential-flow filtration, dialysis, centrifugation, ultracentrifugation, liquid chromatography, including the use of affinity columns or resins. The isolation step can result in different levels of purity. For example, after isolation the engineered influenza polypeptides comprise less than 10%, 5%, 2%, or 1% impurities.

As used herein "engineered" is synonymous with "modified" and means that an influenza polypeptide has one or more differences when compared to the natural sequence of that particular peptide. This difference can be a deletion of one or more amino acids from the $NH_2$-terminal or C-terminal ends, or addition of one or more amino acids to the $NH_2$-terminal or C-terminal ends. The difference can also be a one or more point mutations in a given wild-type influenza polypeptide.

As used herein "about" means with 10% of the stated value.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Engineered Hemagglutinin Polypeptides

Influenza hemagglutinin (HA) protein forms into a homotrimeric complex expressed on the surface of the mature influenza virion. The protein has two major domains: the globular $HA_1$; and the α-helical $HA_2$. $HA_1$ mediates cell entry of influenza by binding to sialic acid on the surface of a target cell. After the cell internalizes the virion into an endosomal/lysosomal compartment, at a pH of about 6.0, the conformation of the HA protein changes so that the $HA_2$ domain anchors the virion into the lipid bilayer of the endosomal compartment, allowing entry into the cytoplasm of the host cell, and viral replication.

Described herein are compositions comprising one or more isolated, engineered influenza polypeptides. The polypeptides are useful for the prophylactic immunization against influenza. In certain embodiments, any of the one or more isolated, engineered influenza polypeptides comprises the HA protein. In certain embodiments, any of the one or more isolated, engineered influenza polypeptides comprises a fragment of the HA protein. In certain embodiments, the fragment of the HA protein is the $HA_1$ domain. In certain embodiments, the $HA_1$ domain fragment can extend into the $HA_2$ domain by 1, 2, 3, 4, 5, 6, 7, 8, 9, 10, 15, or 20 amino acids or less. In certain embodiments, the fragment of the HA protein: (a) comprises an $HA_1$ domain, and (b) does not comprise a $HA_2$ domain or a transmembrane domain. In certain embodiments, the fragment of the HA protein comprises greater than 10 amino acids. In certain embodiments, the fragment of the HA protein comprises greater than 40 amino acids. In certain embodiments, the fragment of the HA protein comprises greater than 50 amino acids. In certain embodiments, the fragment of the HA protein comprises greater than 100 amino acids. In certain embodiments, the fragment of the HA protein comprises less than the 300 amino acids from the $NH_2$-terminus of the HA protein. In certain embodiments, the 300 amino acids from the NH$_2$-terminus of the HA protein lack the influenza signal sequence. In certain embodiments, the fragment of the HA protein does not comprise the HA$_2$ domain. In certain embodiments, the fragment of the HA protein does not comprise a transmembrane domain. In certain embodiments, the fragment of the HA protein comprises an amino acid set forth in any of SEQ ID NOs: 1-20. In certain embodiments, the fragment of the HA protein comprises an HA$_1$ domain with an amino acid sequence at least 80% identical to that set forth in any of SEQ ID NOs: 1-20. In certain embodiments, the fragment of the HA protein comprises an HA$_1$ domain with an amino acid sequence at least 90% identical to that set forth in any of SEQ ID NOs: 1-20. In certain embodiments, the fragment of the HA protein comprises an HA$_1$ domain with an amino acid sequence at least 95% identical to that set forth in any of SEQ ID NOs: 1-20. In certain embodiments, the fragment of the HA protein comprises an HA$_1$ domain with an amino acid sequence at least 97% identical to that set forth in any of SEQ ID NOs: 1-20. In certain embodiments, the fragment of the HA protein comprises an HA$_1$ domain with an amino acid sequence at least 98% identical to that set forth in any of SEQ ID NOs: 1-20. In certain embodiments, the fragment of the HA protein comprises an HA$_1$ domain with an amino acid sequence at least 99% identical to that set forth in any of SEQ ID NOs: 1-20. In certain embodiments, the HA protein has not been modified or mutated at a cysteine residue.

The one or more isolated, engineered influenza polypeptides can be modified in several ways in order to increase immunogenicity of the polypeptide, or to increase yield from a cell-based protein production system. In certain embodiments, the transmembrane domain may be deleted to improve solubility, and/or allow secretion from a cell. In certain embodiments, a signal peptide is attached to the NH$_2$-terminus of any of the influenza polypeptides in order to direct secretion from a cellular protein production system. In certain embodiments, the signal peptide is the yeast alpha factor signal sequence. In certain embodiments, the signal peptide comprises an amino acid sequence set forth in SEQ ID NO: 22. In certain embodiments, the signal peptide comprises an amino acid sequence 80% identical to that set forth in SEQ ID NO: 22. In certain embodiments, the signal peptide comprises an amino acid sequence 90% identical to that set forth in SEQ ID NO: 22. In certain embodiments, the signal peptide comprises an amino acid sequence 95% identical to that set forth in SEQ ID NO: 22. In certain embodiments, the signal peptide comprises an amino acid sequence 98% identical to that set forth in SEQ ID NO: 22. In certain embodiments, the signal peptide comprises an amino acid sequence 99% identical to that set forth in SEQ ID NO: 22. In certain embodiments, the polypeptide comprises one or more purification tags, to facilitate purification of a recombinant polypeptide such as: a poly-histidine tag (e.g., 5-10 histidine residues in length); a 6×HIS tag; a poly-glutamine tag; a c-MYC tag (EQKLISEEDL); a FLAG tag (DYKDDDDK); a V5 tag (GKPIPNPLLGLDST); VSV-tag (YTDIEMNRLGK); an Xpress tag; or any combination thereof. In certain embodiments, the purification tag comprises an amino acid sequence set forth in SEQ ID NO: 21. In certain embodiments, the purification tag is covalently attached to the NH$_2$-terminus of the polypeptide. In certain embodiments, the purification tag is covalently attached to the C-terminus of the polypeptide. In certain embodiments, any of the one or more influenza polypeptides comprises a cleavage site between the HA polypeptide and the purification tag. In certain embodiments, the cleavage site is an enterokinase/enteropeptidase cleavage site. In certain embodiments, any of the one or more isolated, engineered influenza polypeptides consists of an NH$_2$-terminal alpha secretion factor signal peptide, the HA$_1$ domain of an influenza hemagglutinin protein, and a polyhistidine purification tag. In certain embodiments, any of the one or more isolated, engineered influenza polypeptides comprise an NH$_2$-terminal alpha secretion factor signal peptide, the HA$_1$ domain of an influenza hemagglutinin protein with an amino acid sequence set forth in any of SEQ ID NOs:1-20, and a polyhistidine purification tag. In certain embodiments, any of the one or more isolated, engineered influenza polypeptides consist of an NH$_2$-terminal alpha secretion factor signal peptide, the HA$_1$ domain of an influenza hemagglutinin protein set forth in any of SEQ ID NOs:1-20, and a polyhistidine purification tag. In certain embodiments, any of the one or more isolated, engineered influenza polypeptides consists of an NH$_2$-terminal alpha secretion factor signal peptide, the HA$_1$ domain of an influenza hemagglutinin protein, an enterokinase cleavage site (Asp-Asp-Asp-Asp-Lys), and a polyhistidine purification tag. In certain embodiments, any of the one or more isolated, engineered influenza polypeptides consist of an NH$_2$-terminal alpha secretion factor signal peptide, the HA$_1$ domain of an influenza hemagglutinin protein with an amino acid sequence set forth in any of SEQ ID NOs:1-20, an enterokinase cleavage site (Asp-Asp-Asp-Asp-Lys), and a polyhistidine purification tag. In certain embodiments, any of the one or more isolated, engineered influenza polypeptides consist of an HA$_1$ domain of an influenza hemagglutinin protein with an amino acid sequence set forth in any of SEQ ID NOs:1-20, an enterokinase cleavage site (Asp-Asp-Asp-Asp-Lys), and a polyhistidine purification tag. In certain embodiments, any of the one or more isolated, engineered influenza polypeptides consist of an HA$_1$ domain of an influenza hemagglutinin protein with an amino acid sequence set forth in any of SEQ ID NOs:1-20, and an enterokinase cleavage site (Asp-Asp-Asp-Asp-Lys). In certain embodiments, an isolated engineered influenza polypeptide is less than 50 kDa. In certain embodiments, an isolated engineered influenza polypeptide is less than 40 kDa. In certain embodiments, an isolated engineered influenza polypeptide is greater than 10 kDa. In certain embodiments, an isolated engineered influenza polypeptide is greater than 20 kDa. In certain embodiments, an isolated engineered influenza polypeptide is greater than 30 kDa.

Different organisms display different patterns of glycosylation at amino acid residues in proteins. Generally, high-mannose glycans are attached to asparagines in the endoplasmic reticulum (ER) and are modified during subsequent transit through the ER and Golgi apparatus. For proteins that are produced in cellular expression systems, different systems can generate different types of glycans. For example, proteins produced from insect cells tend to lack terminal sialyation. In humans, however, most asparagine linked glycans display modification by terminal sialic acid or N-Acetylneuraminic acid (Neu5Ac) attached to N-acetylglucosamine (GlcNAc). Any of the one or more isolated, engineered influenza polypeptides can be glycosylated in a way that mimics human glycosylation. In certain embodiments, greater than 50% of all N-linked glycans of an isolated, engineered influenza polypeptide comprise a sialic acid or N-Acetylneuraminic acid (Neu5Ac). In certain embodiments, greater than 60% of all N-linked glycans of an isolated, engineered influenza polypeptide comprise a sialic acid or N-Acetylneuraminic acid (Neu5Ac). In certain embodiments, greater than 70% of all N-linked glycans of an isolated, engineered influenza polypeptide comprise a sialic acid. In certain embodiments, greater than 80% of all N-linked glycans of an isolated, engineered influenza polypeptide comprise a sialic acid or N-Acetylneuraminic acid (Neu5Ac). In certain embodiments, greater than 90% of all N-linked glycans of an isolated, engineered influenza polypeptide comprise a sialic acid or N-Acetylneuraminic acid (Neu5Ac).

Strains of Influenza and HA Polypeptides

This disclosure describes a flexible platform for the production of engineered influenza polypeptides which is broadly applicable to any soluble influenza polypeptide or antigen. In a certain embodiment, the compositions of the current disclosure comprise one or more HA polypeptides from any strain currently used in flu vaccine production, or that may occur in association with human disease. In certain embodiments, the composition contains at least one, two, three, four, or five different influenza HA polypeptides, each from a different strain. In certain embodiments, the influenza HA polypeptide may be derived from any H1N1 or H3N2 strain. In certain embodiments, the influenza HA polypeptide may be derived from any H5N1 strain. In certain embodiments, influenza HA polypeptides may be derived from any one, two, three, four, or five of the following strains: A/Moscow/10/1999; A/New_Caledonia/20/1999; B/Sichuan/379/1999; A/Panama/2007/1999; B/Hong_Kong/330/2001; A/Wyoming/03/2003; B/Shanghai/361/2002; A/Wisconsin/67/2005; B/Malaysia/2506/2004; A/Hiroshima/52/2005; B/Ohio/1/2005; A/Solomon Islands/3/2006; A/Brisbane/59/2007; A/Brisbane/10/2007; B/Florida/4/2006; B/Brisbane/60/2008; A/California/7/2009; A/Perth/16/2009; A/Victoria/361/2011; B/Massachusetts/02/2012, and combinations thereof.

Any of the one or more isolated, engineered influenza polypeptides can be linked to a purification tag using a fusion tag cleavage site that facilitate removal of the purification tag from the engineered influenza polypeptide. Fusion tag cleavage sites comprise, for example, an enterokinase cleavage site (Asp-Asp-Asp-Asp-Lys), Facto Xa cleavage site (Ile-Glu or Asp-Gly-Arg-X), HRV3C Protease (Leu-Glu-Val-Leu-Phe-Gln-Gly-Pro-X), TEV Protease (Glu-Asn-Leu-Tyr-Phe-Gln-Gly-X), or a thrombin cleavage site. In certain embodiments, any of the one or more isolated, engineered influenza polypeptides can comprise a remnant of a fusion tag cleavage site, that is the amino acids that remain after an enzyme that cleaves the fusion tag cleavage site. For example, enterokinase specifically cleaves polypeptides at the specific sequence, Asp-Asp-Asp-Asp-Lys-X, with X being any amino acid other than proline, at the C-terminal end of the lysine, making the remnant (Asp-Asp-Asp-Asp-Lys).

Mixtures of Isolated, Engineered Polypeptides

The isolated, engineered influenza polypeptides of the current disclosure are useful for prophylactic vaccination against influenza. Current seasonal influenza vaccines are made up of at least three, and sometimes four different influenza strains. In certain embodiments, described herein, are compositions comprising one or more isolated, engineered influenza polypeptides. In certain embodiments, are compositions comprising two or more isolated, engineered influenza polypeptides. In certain embodiments, are compositions comprising three or more isolated, engineered influenza polypeptides. In certain embodiments, are compositions comprising four or more isolated, engineered influenza polypeptides. In certain embodiments, are compositions comprising five or more isolated, engineered influenza polypeptides. In certain embodiments, described herein, are compositions consisting essentially of one or more isolated, engineered influenza polypeptides. In certain embodiments, are compositions consisting essentially of two or more isolated, engineered influenza polypeptides. In certain embodiments, are compositions consisting essentially of three or more isolated, engineered influenza polypeptides. In certain embodiments, are compositions consisting essentially of four or more isolated, engineered influenza polypeptides. In certain embodiments, are compositions consisting essentially of five or more isolated, engineered influenza polypeptides. In certain embodiments, described herein, are compositions consisting essentially of one or more isolated, engineered influenza polypeptides and an immunological adjuvant. In certain embodiments, are compositions consisting essentially of two or more isolated, engineered influenza polypeptides and an immunological adjuvant. In certain embodiments, are compositions consisting essentially of three or more isolated, engineered influenza polypeptides and an immunological adjuvant. In certain embodiments, are compositions consisting essentially of four or more isolated, engineered influenza polypeptides and an immunological adjuvant. In certain embodiments, are compositions consisting essentially of five or more isolated, engineered influenza polypeptides and an immunological adjuvant. Consisting essentially means that the composition contains the recited constituents plus non-active, inert ingredients that act merely to preserve, stabilize, solubilize, or provide volume and viscosity to the composition without imparting additional antigenicity or immunogenicity to the vaccine.

Cell Based Systems for Production of Engineered Hemagglutinin Polypeptides

The isolated, engineered influenza polypeptides of the current disclosure are purified from a cell based protein production system that has been transformed, transfected, or infected with a nucleic acid encoding an engineered influenza polypeptide. In certain embodiments, the cell based protein production system is stably transformed with the nucleic acid, such that the nucleic acid integrates into at least one chromosome of the cell based protein production system. In certain embodiments, the eukaryotic system is yeast. In certain embodiments, the yeast is a *Pichia pastoris* strain. In certain embodiments, the *Pichia pastoris* strain is GS115, KM71H, SMD1168, BG08, BG, 09, BG10, BG11, or SMD1168H. In certain embodiments, the *Pichia pastoris* strain is GS115. In certain embodiments, the strain of *Pichia pastoris* is modified to produce a human glycosylation pattern in polypeptides produced using the system. In certain embodiments, the strain of *Pichia pastoris* is modified to delete the endogenous yeast glycosylation pathway. In certain embodiments, the yeast comprises a human gene encoding any of mannosidase I, mannosidase II, N-acetylglucosaminyl transferase I, N-acetylglucosaminyl transferase II, and uridine 5'-diphosphate (UDP)-N-acetylglucosamine transporter. In certain embodiments, the strain of *Pichia pastoris* is modified to produce terminal sialyation on N-linked glycans. In certain embodiments, the strain of *Pichia pastoris* is modified to produce terminal sialyation on N-linked glycans. In certain embodiments, the cell based protein purification system does not comprise insect cells. In certain embodiments, the cell based protein purification system does not comprise eggs.

Nucleic Acids Encoding Engineered Hemagglutinin Proteins

The isolated, engineered influenza polypeptides of the current disclosure can be produced in cell based protein production systems that have been modified by nucleic acids to express the engineered influenza polypeptides. Therefore, any of the engineered influenza polypeptides described herein can be encoded by a nucleic acid. In certain embodiments, the nucleic acid is a plasmid. In certain embodiments, the plasmid comprises an origin or replication for propagation in *E. coli*. In certain embodiments, the nucleic acid is encoded on a plasmid suitable for transforming yeast. In certain embodiments, the plasmid is suitable for homologous recombination in yeast. In certain embodiments, the plasmid comprises a gene for a yeast auxotrophy such as histidine, tryptophan, leucine, lysine, methionine, or uracil. In certain embodiments, the plasmid has a gene that confers antibiotic resistance to ampicillin, kanamycin, neomycin, G418, carbenicillin, chloramphenicol, blasticidin, zeocin, or any combination thereof. In a certain embodiment, the plasmid is pPIC9 SHUTTLE. In certain embodiments, the nucleic acid is a linear single or double stranded DNA molecule able to undergo homologous recombination in yeast. In certain embodiments, the nucleic acid is a double stranded linear DNA molecule that comprises any of the engineered influenza polypeptides of the current disclosure. In certain embodiments, the nucleic acid is a PCR product that comprises any of the engineered influenza polypeptides of the current disclosure. In certain embodiments, the nucleic acid comprises a sequence that encodes any of the polypeptides set forth in SEQ ID NOs:1-20. In certain embodiments, the nucleic acid comprises a sequence that encodes any of the polypeptides set forth in SEQ ID NOs: 1-20. In certain embodiments, the nucleic acid comprises a sequence that encodes a polypeptide with an amino acid sequence at least 80% identical to that set forth in any of SEQ ID NOs: 1-20. In certain embodiments, the nucleic acid comprises a sequence that encodes a polypeptide with an amino acid sequence at least 90% identical to that set forth in any of SEQ ID NOs: 1-20. In certain embodiments, the nucleic acid comprises a sequence that encodes a polypeptide with an amino acid sequence at least 95% identical to that set forth in any of SEQ ID NOs: 1-20. In certain embodiments, the nucleic acid comprises a sequence that encodes a polypeptide with an amino acid sequence at least 97% identical to that set forth in any of SEQ ID NOs: 1-20. In certain embodiments, the nucleic acid comprises a sequence that encodes a polypeptide with an amino acid sequence at least 98% identical to that set forth in any of SEQ ID NOs: 1-20. In certain embodiments, the nucleic acid comprises a sequence that encodes a polypeptide with an amino acid sequence at least 99% identical to that set forth in any of SEQ ID NOs: 1-20. In certain embodiments, the engineered influenza polypeptide is encoded by a nucleic acid that has been codon optimized for expression in yeast.

Subjects for Vaccination

In certain embodiments, the one or more isolated, engineered influenza polypeptides are administered to an individual in order to induce a primary immune response in the individual. In certain embodiments, the individual is a human, pig, or chicken. In certain embodiments, the individual is a human. In certain embodiments, the one or more isolated, engineered influenza polypeptides are administered to an individual previously subject to influenza vaccination in order to boost an immune response in the individual previously subject to influenza vaccination. In certain embodiments, the one or more isolated, engineered influenza polypeptides are administered to an individual with at least one risk factor associated with influenza related mortality such as a child under 2 years of age, a pregnant woman, an immunocompromised individual, an individual afflicted with COPD/emphysema, an individual over the age of 65, a person diagnosed with HIV, a person receiving chemotherapy or radiation therapy, or a person with a genetic immunodeficiency disorder, such as X-SCID. In certain embodiments, the one or more isolated, engineered influenza polypeptides are administered to an individual with an egg allergy. In certain embodiments, the one or more isolated, engineered influenza polypeptides are administered to an individual with a severe egg allergy. In certain embodiments, the one or more isolated, engineered influenza polypeptides are suitable for administration to an individual with a severe egg allergy. In certain embodiments, the one or more isolated, engineered influenza polypeptides are administered to an individual mixed with an immunological adjuvant. In certain embodiments, the one or more isolated, engineered influenza polypeptides are administered to an individual mixed with a pharmaceutically acceptable vehicle, carrier, or excipient.

Dosage Schedules and Amounts

In certain embodiments, the one or more isolated, engineered influenza polypeptides of the current disclosure are formulated as a liquid for administration via an intramuscular injection. In certain embodiments, the liquid form is formulated in single use vials or syringes. In certain embodiments, the liquid form is lyophilized and can be reconstituted with a suitable liquid such as sterile water or saline. In certain embodiments, the liquid form is formulated for a dose of between 0.1 and 1.0 mL. In certain embodiments, the liquid form is formulated for a dose of between 0.2 and 0.8 mL. In certain embodiments, the liquid form is formulated for a dose of between 0.4 and 0.6 mL. In certain embodiments, the liquid form is formulated for a dose of about 0.5 mL. In certain embodiments, the concentration of any of the isolated, engineered influenza polypeptides is between 1 μg/mL and 100 μg/mL. In certain embodiments, the concentration of any of the isolated, engineered influenza polypeptides is between 10 μg/mL and 100 μg/mL. In certain embodiments, the concentration of any of the isolated, engineered influenza polypeptides is between 40 μg/mL and 60 μg/mL. In certain embodiments, the concentration of any of the isolated, engineered influenza polypeptides is greater than 1 μg/mL. In certain embodiments, the concentration of any of the isolated, engineered influenza polypeptides is greater than 10 μg/mL. In certain embodiments, the concentration of any of the isolated, engineered influenza polypeptides is greater than 20 μg/mL. In certain embodiments, the concentration of any of the isolated, engineered influenza polypeptides is greater than 40 μg/mL. In certain embodiments, the concentration of any of the isolated, engineered influenza polypeptides is less than 100 μg/mL. In certain embodiments, the concentration of any of the isolated, engineered influenza polypeptides is less than 80 μg/mL. In certain embodiments, the concentration of any of the isolated, engineered influenza polypeptides is less than 60 μg/mL. In certain embodiments, any of the isolated, engineered influenza polypeptides are administered seasonally or once a year. In a certain embodiment, the one or more isolated, engineered influenza polypeptides of the current disclosure are administered to a subject in a therapeutically or prophylactically acceptable amount. A prophylactically acceptable amount is one that induces an antibody response sufficient to prevent or lessen the impact of a subsequent natural infection with an influenza strain corresponding to the one used for immunization. The prophylactically acceptable amount can vary depending on the exact strain or immunological adjuvant used in the isolated, engineered influenza polypeptide composition.

Immunological Adjuvants In certain embodiments, described herein, are compositions of matter that comprise one or more isolated, engineered influenza polypeptides and an immunological adjuvant in an amount effective to enhance an immune response. In certain embodiments, the adjuvant comprises an adjuvant currently used in flu vaccination, such as MF59, an oil-in-water emulsion using squalene. In certain embodiments, the adjuvant is a mineral salt. In certain embodiments, the adjuvant comprises alum salt. In certain embodiments, the adjuvant comprises aluminum phosphate or aluminum hydroxide. In certain embodiments, the adjuvant comprises Quil A or saponin QS-21. In certain embodiments, the adjuvant comprises N-acetyl muramyl-L-alanyl-D-isoglutamine (MDP). In certain embodiments, the adjuvant comprises a Freund's adjuvant, such as CFA or IFA; Montanide; Adjuvant 65; Lipovant; or any combination thereof. In certain embodiments, the adjuvant comprises a cytokine such as interferon gamma or GM-CSF. In certain embodiments, described herein, the adjuvant comprises one or more Toll-like receptor (TLR) ligands. In certain embodiments, the TLR ligand is LPS or a CpG oligonucleotide. In certain embodiments, the TLR ligand activates signaling through any one of TLR2, TLR3, TLR4, TLR5, TLR6, TLR7, TLR8, or TLR9.

Pharmaceutically Acceptable Vehicle, Carrier, or Excipient

In certain embodiments, described herein, are compositions of matter that comprise one or more isolated, engineered influenza polypeptides and a pharmaceutically acceptable vehicle, carrier, or excipient. In certain embodiments, the pharmaceutically acceptable vehicle, carrier, or excipient comprises a pH buffer or pH modifier. In certain embodiments, the pH buffer or pH modifier comprises sodium bicarbonate, HEPES, MOPS, MEPES, phosphate buffer, succinate buffer, citric acid, ascorbic acid, or any combination thereof. In certain embodiments, the pharmaceutically acceptable vehicle, carrier or excipient comprises a salt solution. In certain embodiments, the salt solution comprises sodium chloride, potassium chloride, calcium chloride, hemin chloride, benzethonium chloride, or any combination thereof. In certain embodiments, the pharmaceutically acceptable vehicle, carrier or excipient comprises a carbohydrate. In certain embodiments, the carbohydrate comprises sucrose, dextrose, trehalose, lactose, cellulose, sorbitol, galactose, dextran, xanthan, or any combination thereof. In certain embodiments, the pharmaceutically acceptable vehicle, carrier or excipient comprises an amino acid or protein. In certain embodiments, the amino acid or protein comprises gelatin, egg protein, yeast extract, glutamate, albumin, In certain embodiments, the pharmaceutically acceptable vehicle, carrier or excipient comprises an emulsifier. In certain embodiments, the emulsifier comprises octylphenol ethoxylate (Triton X-100), polysorbate 20, polysorbate 80 (Tween 80), sodium deoxy cholate, or any combination thereof. In certain embodiments, the pharmaceutically acceptable vehicle, carrier or excipient comprises a chelating agent. In certain embodiments, the chelating agent comprises ethylene diamine tetra acetic acid sodium (EDTA), EGTA, or any combination thereof. In certain embodiments, the carrier is poly D,L-lactide-co-glycolide (PLGA).

Master Cell Bank and Transgenic Yeast

In a certain embodiment, described herein is a master cell bank comprising a yeast that comprises a nucleic acid encoding one or more influenza polypeptides integrated into its genome creating a transgenic yeast strain. In some embodiments, the master cell bank comprises a plurality of yeast cells that each comprise a nucleic acid encoding an influenza polypeptide from a different strain of influenza integrated into its genome creating a transgenic yeast strain. In certain embodiments, the influenza polypeptide is an engineered polypeptide comprising an $HA_1$ domain. In certain embodiments, the influenza polypeptide (a) comprises a hemagglutinin $HA_1$ domain; and (b) does not comprise a hemagglutinin $HA_2$ domain or a transmembrane domain. In certain embodiments, the nucleic acid is maintained extra-chromosomally on a plasmid or yeast artificial chromosome. In certain embodiments, the nucleic acid is integrated into a chromosomal location. In certain embodiments, the yeast is *Pichia pastoris*. In certain embodiments, the *Pichia pastoris* is a GS115 strain. In certain embodiments, the transgenic yeast is created by transformation with linearized plasmid, a PCR product, or a synthesized double stranded DNA molecule. In certain embodiments, the transgenic yeast is created by homologous recombination. In certain embodiments, the master cell bank comprises a cryopreservative suitable for freezing to at least about −80° or below. In certain embodiments, the master cell bank comprises glycerol at between 10 and 30%, and is suitable for long term storage at about −80° or below. In certain embodiments, the master cell bank can preserve a transgenic yeast strain for at least 1, 2, 3, 4, 5, 6, 7, 8, 9, 10 or more years.

EXAMPLES

The following examples are for illustrative purposes and do not serve to restrict the scope of this disclosure.

Example 1—Yeast Production of an Isolated, Engineered Influenza Polypeptide for Use in Vaccination Against the Influenza Virus Referring to FIG. 1, in step I, a suitable influenza polypeptide is selected for further modification and molecular engineering 1. A schematic of an exemplary engineered hemagglutinin polypeptide is shown in FIG. 2. In this case, the $HA_1$ domain of a full-length hemagglutinin polypeptide is defined. Optionally, the structure of the defined $HA_1$ domain can be checked using protein structure modeling software, such as Swiss-Model. See Arnold et al. "The SWISS-MODEL Workspace: A web-based environment for protein structure homology modelling," *Bioinformatics,* 22, 195-201. If the overall tertiary structure of the $HA_1$ polypeptide fragment is not preserved, the polypeptide can be further modified by deleting or adding residues from the original full-length hemagglutinin polypeptide to better preserve structure after expression. In any case, this $HA_1$ domain will lack the influenza signal sequence and the transmembrane domain of the full-length HA protein, and a substantial portion of the $HA_2$ domain. This should leave a soluble antigenic $HA_1$ polypeptide.

After the antigenic $HA_1$ sequence is determined, a full construct can be engineered that allows for efficient production of the polypeptide in a yeast system. First, a polyhistidine sequence consisting of 6 histidine residues is added, and optionally, an enterokinase cleavage site (DDDDK) is added between the HA polypeptide sequence and the polyhistidine tag. The enterokinase cleavage site allows removal of the polyhistidine tag after or during purification so that the tag will not be present in the final polypeptide preparation. Additionally, a secretory leader sequence, such as the yeast alpha factor signal peptide, is added to the $NH_2$-terminus in order to direct secretion from yeast. After this step the amino acid sequence should comprise a fully soluble HA₁ sequence, which lacks both the HA₂ and transmembrane domains, and the endogenous HA signal sequence; with the addition of an NH₂-terminal alpha factor secretory leader and a C-terminal 6×HIS purification tag, that is separated from the fully soluble HA₁ sequence by an enterokinase cleavage site. After the amino acid sequence of the polypeptide is determined, a DNA sequence is reverse translated from this amino acid sequence, and optionally, the sequence may be codon optimized resulting in high expression levels in yeast. Restriction sites are then added to flank the full construct for ease of cloning into a shuttle vector. The DNA sequence can then be synthesized by methods that are known in the art and commercially available.

After synthesis, the DNA encoding the engineered HA₁ polypeptide is cloned into a shuttle vector that facilitates homologous recombination in yeast (e.g., pPIC9 SHUTTLE). Briefly, the DNA encoding the engineered HA₁ polypeptide is digested with restriction enzymes and ligated into a shuttle vector (i.e., plasmid vector) that has been digested with the same enzymes. After the ligation reaction is carried out the ligated shuttle plasmid/engineered HA₁ polypeptide DNA is transformed into $E.\ coli$ (e.g., DH5α), and transformed bacteria are selected using plates containing a selective antibiotic corresponding to an antibiotic resistance gene in present in the shuttle plasmid/engineered HA₁ polypeptide (e.g., Kanamycin). The plates are incubated at 37° overnight, and colonies that grow under antibiotic selection are chosen for further analysis. Colonies are then grown in liquid culture to high density, and plasmid DNA is prepared using the alkaline lysis method. The plasmid DNA can then be analyzed by restriction mapping, PCR, or sequencing to verify the accuracy of the DNA encoding the engineered HA₁ polypeptide.

Referring to FIG. 1, step II, once the shuttle plasmid encoding the engineered HA₁ polypeptide is designed, constructed and prepared it can be introduced into a suitable yeast system by cell engineering 2. The shuttle plasmid is linearized by restriction enzyme digestion and transformed into yeast where it stably integrates into the genome by homologous recombination. The *Pichia pastoris* strain GS115 is grown at 30° in 500 mL of rich media (e.g., YPD) to log phase at an O.D of 1.5 at 590 nm, harvested, washed and resuspended in 1 mL of 1M sorbitol. The yeast cells are then transformed by electroporation using 20 µg of linearized shuttle plasmid encoding the engineered HA₁ polypeptide at 1500 V, 25 µF, 200Ω over 5-10 seconds with an electrode gap of 0.2 cm. The cells are then grown in a dextrose based recovery media, and plated on minimal media corresponding to an auxotrophy of GS115 strain and selection marker present on the linearized shuttle plasmid encoding the engineered HA₁ polypeptide (e.g., Histidine). This first round of selection results in GS115 clones that have at least one integrated a copy of the linearized shuttle plasmid encoding the engineered HA₁ polypeptide.

After the first round of selection, GS115 clones are selected that have integrated multiple copies of the plasmid in a second round of selection. Selection for the first selection marker (histidine), is followed by selection for a second marker present on the linearized shuttle plasmid encoding the engineered HA₁ polypeptide (the ability metabolize methanol). After GS115 clones have been selected on minimal media lacking histidine, the clones are re-plated on histidine minimal media with the addition of methanol to select for clones that are able to grow in the presence of methanol. In this step multiple different selections can be carried out at different concentrations of methanol to select for GS115 that are more or less sensitive to methanol, and should express different levels of the engineered HA polypeptides. From this second round of selection clones are selected and tested for expression and secretion of the engineered HA₁ polypeptide. This can be done using any suitable protein analysis technique such as SDS-PAGE, ELISA, or Western blot.

Figure 3:
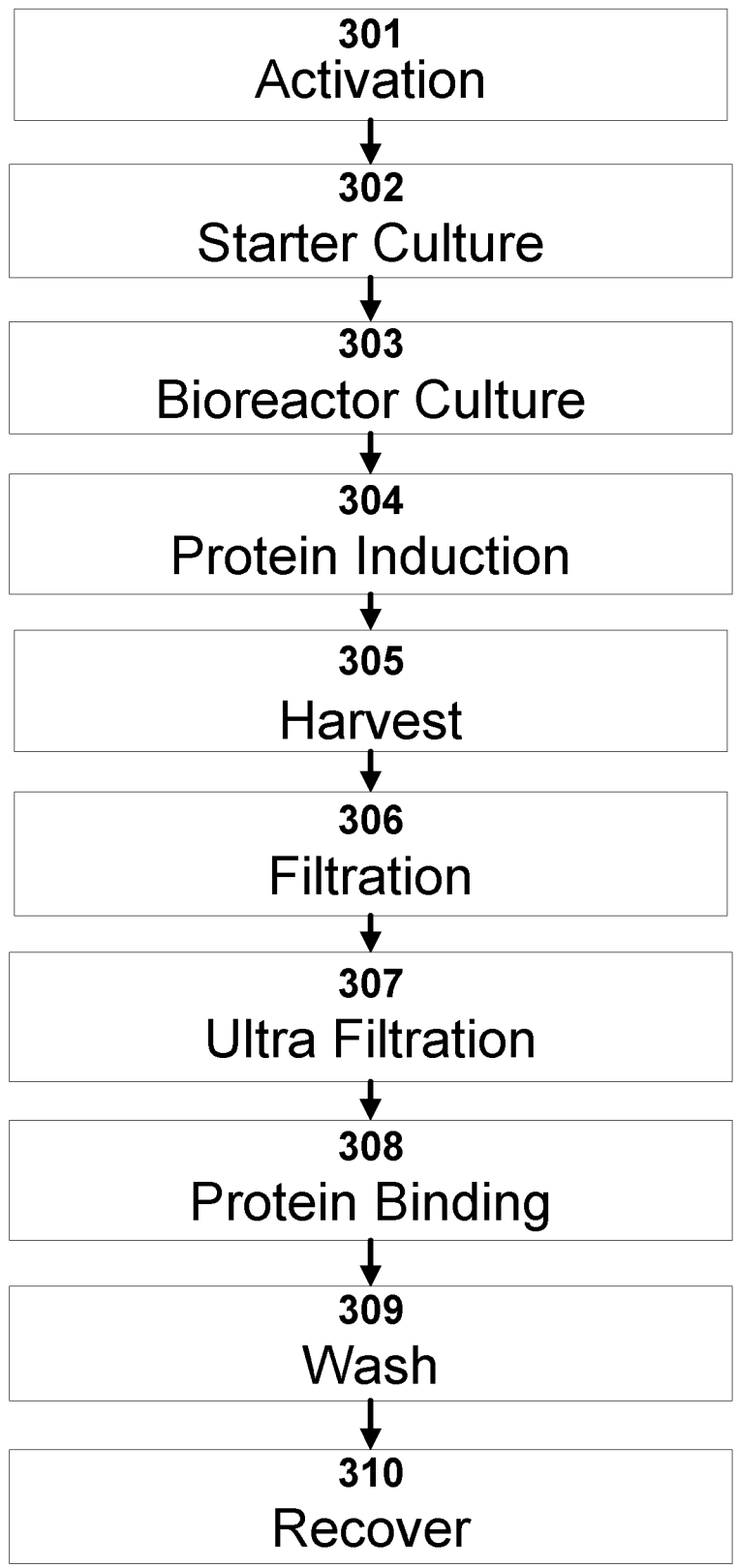
FIG. 3 illustrates a process flowchart depicting steps taken during isolation/purification of an engineered hemagglutinin of this disclosure.

Referring to FIG. 1, Step III, selected GS115 clones can be chosen and scaled-up for large scale protein isolation and purification in a bioprocess engineering step 3. FIG. 3 elaborates steps in the purification. For example, GS115 clones can be thawed from a cryopreserved frozen stock 301, grown in a low volume starter culture 302 and expanded using a using a fed-batch reactor system 303 with a methanol gradient at a rate of 3.6 mL/h/L to 10.9 mL/h/L in 64 hours. After achieving a maximum cell density supernatants can be harvested by centrifugation 305, the supernatants are filtered 306 to remove cellular debris, then subjected to ultrafiltration 307 to remove high molecular weight protein aggregates or low molecular components. The engineered influenza HA polypeptide can be loaded onto a nickel column 308, and unbound or weakly bound proteins and cellular components can be washed at step 309 virtue of the 6×HIS tag. Polypeptides can be eluted from the column 310 using an imidazole gradient, or by cleavage of the enterokinase cleavage site, yielding a recombinant influenza antigen 4.

Alternatively, a "frozen stock" or "master cell bank" can be created by freezing GS115 clones in 20-30% glycerol, and storing at −80° C. or below. This facilitates rapid production of vaccines by allowing for immediate thawing and scale up of clones that have already been selected for optimal expression and efficient production.

Figure 4:
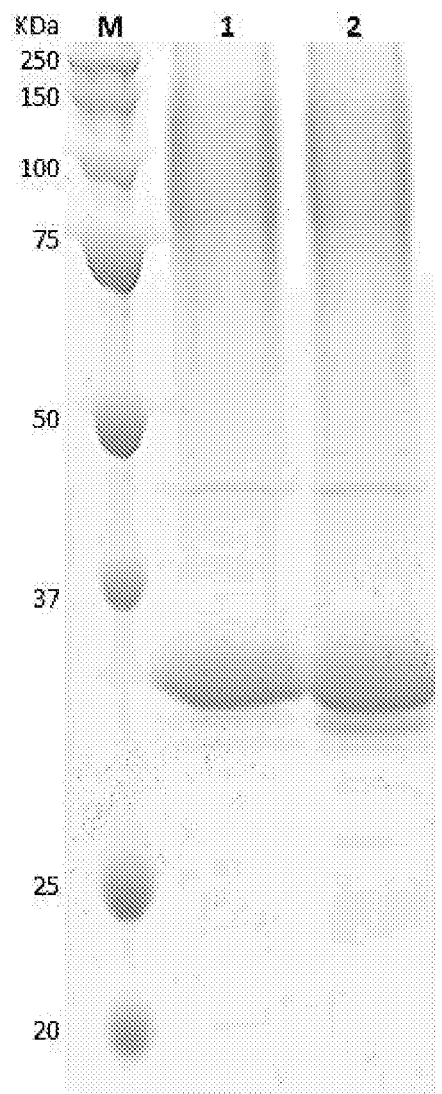
FIG. 4 shows a coomassie stained SDS-PAGE gel of isolated, engineered hemagglutinin polypeptides.

Example 2—Yeast Production of an Isolated, Engineered Influenza Polypeptide for Use in Vaccination Against the Influenza Virus Purification by IMAC FIGS. 4 through 6 show influenza polypeptides produced by the methods described herein. The purification process was started after 84 hours of induction, the sample was centrifuged at 20,000 g at 4° C. for 20 minutes, afterwards the supernatant was concentrated in a Pellicon XL Ultrafiltration Module Biomax (Millipore, Darmstaddt, Germany) with a pore size of 10 kDa. The concentrated solution was filtered through a membrane of 0.45 µm (Pall Corporation, USA) and stored at 4° C. for further processing in IMAC columns. The purifications were carried out on an IMAC pre-packed chromatographic column: 1 and 5 mL His Trap FF (GE Healthcare, UK) and processed as follows: the supernatant was poured into a previously equilibrated Ni+ column. PBS was used as a mobile phase. The supernatant was washed with 10 mL of PBS, followed by another wash with 10 mL PBS+10 mM Imidazole. The protein was eluted with 10 mL of PBS+500 mM Imidazole, the eluted volume was filtered through a 10 kDa membrane (Amicon, Millipore, Darmstadt, Germany) to salt the sample out. The process was repeated tree times and finally the concentration of HA was evaluated with nanodrop (Thermo Scientific, Waltham, Mass., USA), and Bradford assay (Pierce™ Coomassie Bradford Protein Assay Kit, Life Technologies), and visualized in an SDS-PAGE gel.

SDS-PAGE Analysis

Figure 5A:
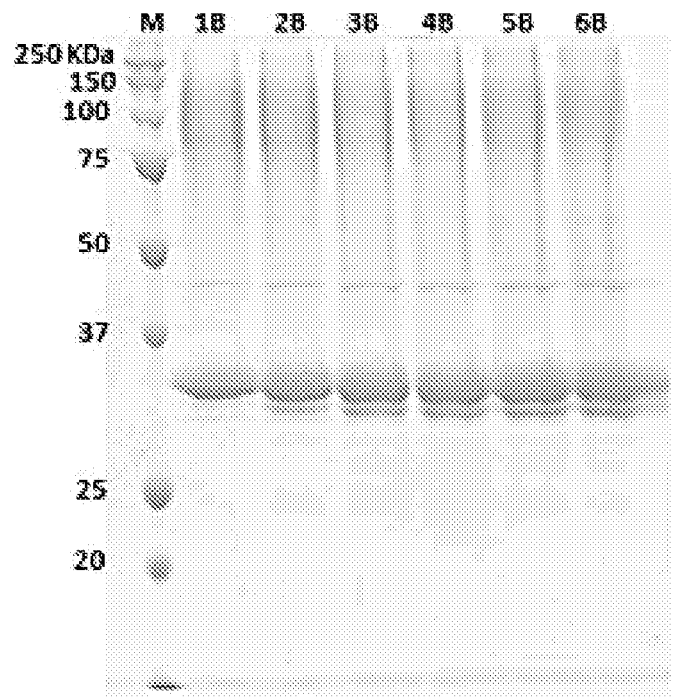
FIG. 5A shows a coomassie stained SDS-PAGE gel of engineered hemagglutinin polypeptides in supernatant taken after 12 hours of bioreactor culture.
Figure 6A:
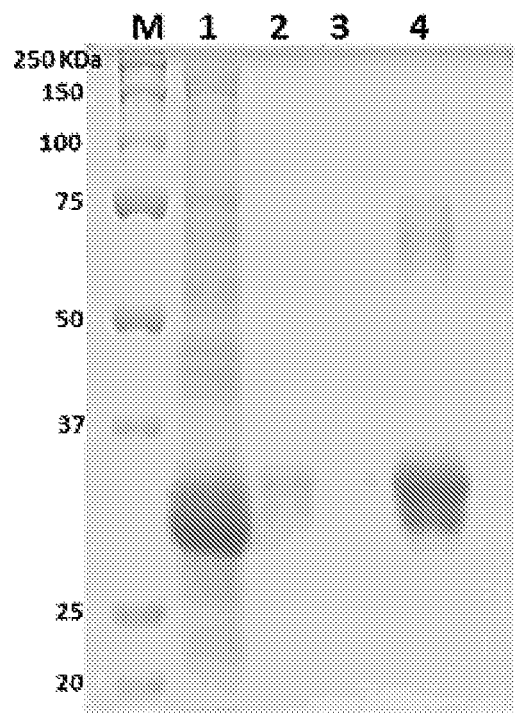
FIG. 6A shows a coomassie stained SDS-PAGE gel of engineered hemagglutinin polypeptides before purification (lane 1) and after (lane 4); lane 2 depicts engineered hemagglutinin polypeptide from the flow through obtained from loading of the Ni column; and lane 3 depicts engineered hemagglutinin polypeptide obtained from the wash steps of the Ni column.

Protein production and purification processes were verified by SDS-PAGE using the standard Laemmli method. For the *P. pastoris* clone samples, 100 µL of supernatant of each clone was concentrated with the Methanol-Chloroform method and the pellets were dried in a Speed Vac Concentrator (Savant Instruments Inc., Farmingdale, N.Y., USA); the samples were resuspended in 10 µL of miliQ water and 10 µL of loading buffer, denatured and used for electrophoresis analysis. The gels were stained with Coomassie brilliant blue R250 (Bio-Rad, Hercules, Calif.), and scanned with an Image Scanner III (GE Healthcare, Amersham, UK). The resulting image was analyzed with densitometry software on TotalLab (TotalLab, Biostat, Jahnsdorf, Germany). FIG. 4 shows Coomassie staining for total protein post purification from 2 different yeast strains expressing engineered hemagglutinin proteins showing high levels of expression. The engineered hemagglutinin proteins are the dark band at approximately 30 kDa. FIG. 5A shows Coomassie staining for total protein post purification from yeast strains expressing engineered hemagglutinin proteins taken at 12 hours post induction. FIG. 6A shows Coomassie staining for total protein post purification from a yeast strain before purification (lane 1) and after (lane 4); lane 2 depicts engineered hemagglutinin polypeptide from the flow through obtained from loading of the nickel column; and lane 3 depicts engineered hemagglutinin polypeptide obtained from the wash steps of the nickel column. Lane 4 shows a highly pure hemagglutinin polypeptide preparation.

Western Blot

Figure 5B:
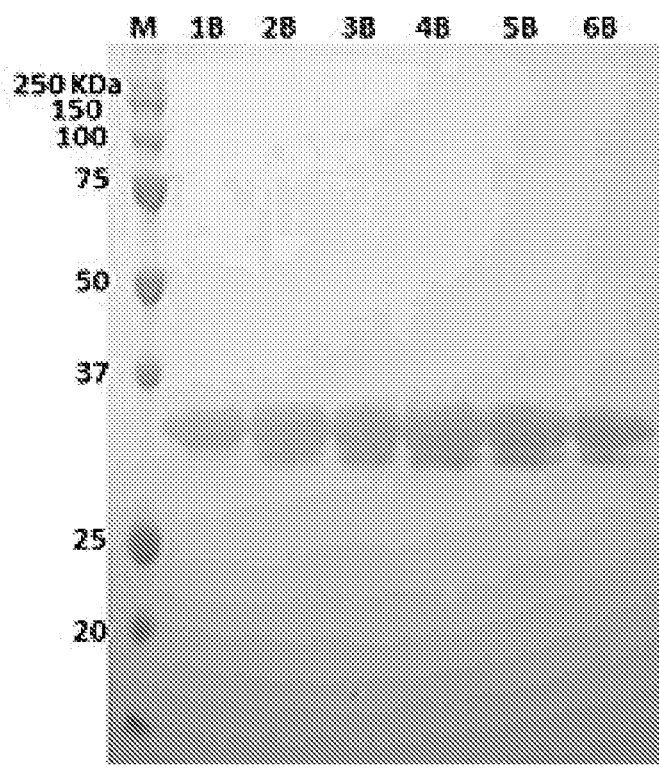
FIG. 5B shows a western blot of engineered hemagglutinin polypeptides in supernatant taken after 12 hours of bioreactor culture.
Figure 6B:
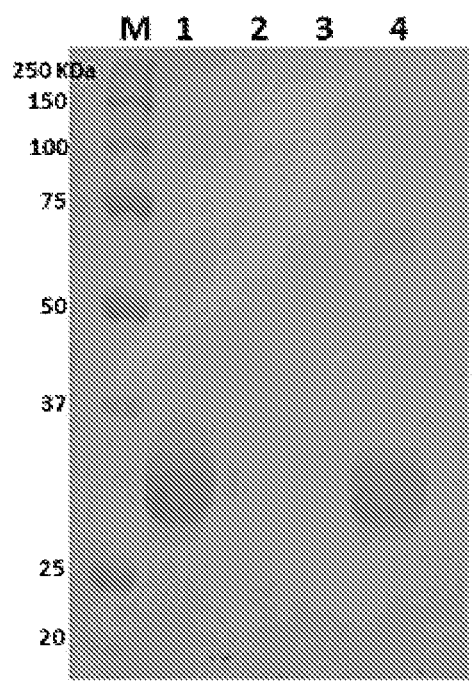
FIG. 6B shows a western blot of engineered hemagglutinin polypeptides before purification (lane 1) and after (lane 4); lane 2 depicts engineered hemagglutinin polypeptide from the flow through obtained from loading of the Ni column; and lane 3 depicts engineered hemagglutinin polypeptide obtained from the wash steps of the Ni column.

The western blot analysis was performed according to standard protocols, the samples collected from the Erlenmeyer flasks were loaded into the Western Blot, with the same concentration as the samples loaded on the SDS-PAGE. The purity of both of the HA obtained from *P. pastoris* could be verified. The samples were loaded at a concentration of 1 g/L and run on an SDS-PAGE gel at 10% and then transferred to a nitrocellulose Hybond-ECL membrane (Amercham Biosciences, UK). The membrane was then blocked for an hour with a solution of PBS and skim milk at 3%. Then the membrane was washed 3 times with the washing buffer, PBS-Tween 20 (1:1000). The membrane was then immersed in a solution with an anti-His antibody at a dilution 1:100 in 1×PBS and incubated for 1 hour at 25° C. and 100 rpm. Three more washes were made, the secondary labeled with horseradish peroxidase (PIERCE®, Thermo Scientific, Waltham, Mass., USA) was added at 1:10,000 dilution in PBS. For immune staining, color was developed by adding Tetra methyl-bencinidyn (Thermo Scientific, Waltham, Mass., USA), finally the membrane was photographed with a Canon EOS 450D camera. FIG. 5B shows western blot for engineered hemagglutinin protein taken at 12 hours post induction. FIG. 6B shows western blot for engineered hemagglutinin protein before purification (lane 1) and after (lane 4); lane 2 depicts engineered hemagglutinin polypeptide from the flow through obtained from loading of the nickel column; and lane 3 depicts engineered hemagglutinin polypeptide obtained from the wash steps of the nickel column.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

SEQUENCES

SEQ ID NO: 1
>A/Moscow/10/1999_(B_C_D_)
STGRICDSPHQILDGENCTLIDALLGDPHCDGFQNKEWDLFVERSKAYSN
CYPYDVPDYASLRSLVASSGTLEFNNESFNWTGVAQNGTSSACKRRSIKS
FFSRLNWLHQLENRYPALN
VTMPNNDKFDKLYIWGVHHPSTDSVQTSVYVQASGRVTVSTKRSQQTVIP
NIGSRPWVRGVSSRISIYWTIVKPGDILLINSTGNLIAPRGYFKIRSGKS
SIMRS SEQ ID NO: 2
>A/New_Caledonia/20/1999_(B_C_D_E_F_G)
GIAPLQLGNCSVAGWILGNPECELLISKESWSYIVETPNPENGTCYPGYF
ADYEELREQLSSVSSFERFEIFPKESSWPNHTVTGVSASCSHNGKSSFYR
NLLWLTGKNGLYPNLSKSYVNNKEKEVLVLWGVHHPPNIGNQRALYHTEN
AYVSVVSSHYSRRFTPEIAKRPKVRDQEGRINYYWTLLEPGDTIIFEANG
NLIAPWYAFALSRGFGSGIITSNA SEQ ID NO: 3
>B/Sichuan/379/99(B)
TRGKLCPTCLNCTDLDVALGRPMCVGITPSAKASILHEIKPVTSGCFPIM
HDRTKIRQLPNLLRGYEKIRLSTQNVINAEKAPGGPYRLGTSGSCPNATS
KSGFFATMAWAVPRDNNKTAT
NPLTVEVPHICTKEEDQITVWGFHSDDKTQMKNLYGDSNPQKFTSSANGI
TTHYVSQIGGFPDQTEDGGLPQSGRIVVDYMVQKPGKTGTIVYQRGILLP
QKV SEQ ID NO: 4
>A/Panama/2007/1999(_C_D_)
STGRICDSPHQILDGENCTLIDALLGDPHCDGFQNKEWDLFVERSKAYSN
CYPYDVPDYASLRSLVASSGTLEFNNESFNWTGVAQNGTSSACKRRSNKS
FFSRLNWLHQLNYKYPALNVTMPNNEKFDKLYIWGVLHPSTDSDQISLYA
QASGRVTVSTKRSQQTVIPNIGSRPWVRGVSSRISIYWTIVKPGDILLIN
STGNLIAPRGYFKIRSGKSSIMRS SEQ ID NO: 5
>B/Hong_Kong/330/2001_(_C_D_)
KTRGKLCPKCLNCTDLDVALGRPKCTGNIPSAKVSILHEVRPVTSGCFPI
MHDRTKIRQLP
NLLRGYERIRLSNHNVINAEKAPGGPYKIGTSGSCPNVTNGNGFFATMAW
AVPKNENNKTATNSLTIEVPYICTEGEDQITVWGFHSDSETQMAKLYGDS
KPQKFTSSANGVTTHYVSQIGGFPNQTEDGGLPQSGRIVVDYMVQKSGKT
GTITYQRGILLPQ SEQ ID NO: 6
>A/Wyoming/03/2003_(E_)
STGGICDSPHQILDGENCTLIDALLGDPQCDGFQNKKWDLFVERSKAYSN
CYPYDVPDYASLRSLVASSGTLEFNNESFNWAGVTQNGTSSACKRRSNKS
FFSRLNWLTHLKYKYPALNVTMPNNEKFDKLYIWGVHHPVTDSEQISLYA
QASGRITVSTKRSQQTVIPNIGYRPRVRDISSRISIYWTIVKPGDILLIN
STGNLIAPRGYFKIRSGKSSIMRS SEQ ID NO: 7
>B/Shanghai/361/2002_(_E_F)
TDLDVALGRPMCVGTTPSAKASILHEVRPVTSGCFPIMHDRTKIRQLPNL
LRGYENIRLSTQNVIDAEKALGGPYRLGTSGSCPNATSKSGFFATMAWAV
PKDNNKNATNPLTVEVPYICT
EGEDQITVWGFHSDDKTQMKNLYGDSNPQKFTSSANGVTTHYVSQIGGFP
DQTEDGGLPQSGRIVVDYMVQKPGKTGTIVYQRGVLLPQKVWCASGRSKV
IKG SEQ ID NO: 8
>A/Wisconsin/67/2005_(_G_H)
STGGICDSPHQILDGENCTLIDALLGDPQCDGFQNKKWDLFVERSKAYSN
CYPYDVPDYASLRSLVASSGTLEFNDESFNWTGVTQNGTSSCKRRSNNS
FFSRLNWLTHLKFKYPALN
VTMPNNEKFDKLYIWGVHHPVTDNDQIFLYAQASGRITVSTKRSQQTVIP
NIGSRPRIRNIPSRISIYWTIVKPGDILLINSTGNLIAPRGYFKIRSGKS
SIMRS SEQ ID NO: 9
>B/Malaysia/2506/2004_(_G_H)
ETRGKLCPKCLNCTDLDVALGRPKCTGNIPSARVSILHEVRPVSGCFPIM
HDRTKIRQLPNLLRGYEHIRLSTHNVINAENAPGGPYKIGTSGSCPNVTN
GNGFFATMAWAVPKNDNNK
TATNSLTIEVPYICTEGEDQITVWGFHSDNEXQMAKLYGDSKPQKFTSSA
NGVTTHYVSQIGGFPNQTEDGGLPQSGRIVVDYMVQKSGKTGTITYQRGI
LLPQ

SEQUENCES

SEQ ID NO: 10
>A/Hiroshima/52/2005_(G)
STGGICDSPHQILDGENCTLIDALLGDPQCDGFQNKKWDLFVERSKAYSN
CYPYDVPDYASLRSLVASSGTLEFNNESFNWTGVTQNGTSSACKRRSNNS
FFSRLNWLTQLKFKYPALK
VTMPNNEKFDKLYIWGVHHPVTDNDQIFLYAQASGRITVSTKRSQQTVIP
NIGSRPRVRNIPSRISIYWTIVKPGDILLINSTGNLIAPRGYFKIRSGKS
SIMRS SEQ ID NO: 11
>B/Ohio/1/2005_(G)
LDVALGRPKCTGNIPSAEVSILHEVRPVTSGCFPIMHDRTKIRQLPNLLR
GYEHIRLSTHNVINAEKAPGGPYKIGTSGSCPNVTNGNGFFATMAWAVPK
NDNNKTATNSLTIEVPYICTE
GEDQITIWGFHSDSETQMAKLYGDSKPQKFTSSANGVTTHYVSQIGGFPN
QTEDGGLPQSGRIVVDYMVQKSGKTGTITYQRGILLPQKVWCASGRSKVI
KGS SEQ ID NO: 12
>A/Solomon_Islands/3/2006_(H)
GIAPLQLGNCSVAGWILGNPECELLISRESWSYIVEKPNPENGTCYPGHF
ADYEELREQLSSVSSFERFEIFPKESSWPNHTTTGVSASCSHNGESSFYK
NLLWLTGKNGLYPNLSKSYANNKEKEVLVLWGVHHPNIGDQRALYHTEN
AYVSVVSSHYSRKFTPEIAKRPKVRDREGRINYYWTLLEPGDTIIFEANG
NLIAPRYAFALSRGFGSGIINSNA SEQ ID NO: 13
>A/Brisbane/59/2007_(I_J_)
GIAPLQLGNCSVAGWILGNPECELLISKESWSYIVEKPNPENGTCYPGHF
ADYEELREQLSSVSSFERFEIFPKESSWPNHTVTGVSASCSHNGESSFYR
NLLWLTGKNGLYPNLSKSYANNKEKEVLVLWGVHHPNIGNQKALYHTEN
AYVSVVSSHYSRKFTPEIAKRPKVRDQEGRINYYWTLLEPGDTIIFEANG
NLIAPRYAFALSRGFGSGIINSNA SEQ ID NO: 14
>A/Brisbane/10/2007_(_I_J)
STGEICDSPHQILDGENCTLIDALLGDPQCDGFQNKKWDLFVERSKAYSN
CYPYDVPDYASLRSLVASSGTLEFNNESFNWTGVTQNGTSSACIRRSNNS
FFSRLNWLTHLKFKYPALNVTMPNNEKFDKLYIWGVHHPGTDNDQIFLYA
QASGRITVSTKRSQQTVIPNIGSRPRVRNIPSRISIYWTIVKPGDILLIN
STGNLIAPRGYFKIRSGKSSIMRS SEQ ID NO: 15
>B/Florida/4/2006_(I)
RTRGKLCPDCLNCTDLDVALGRPMCVGTTPSAKASILHEVKPVTSGCFPI
MHDRTKIRQLPNLLRGYENIRLSTQNVIDAEKAPGGPYRLGTSGSCPNA
TSKSGFFATMAWAVPKDNNKN
ATNPLTVEVPYICTEGEDQITVWGFHSDDKTQMKNLYGDSNPQKFTSSAN
GVTTHYVSQIGSFPDQTEDGGLPQSGRIVVDYMMQKPGKTGTIVYQRGVL
LPQK SEQ ID NO: 16
>B/Brisbane/60/2008_(_J_K_L_M_N_O_P_)
ETRGKLCPKCLNCTDLDVALGRPKCTGKIPSARVSILHEVRPVTSGCFPI
MHDRTKIRQLPNLLRGYEHIRLSTHNVINAENAPGGPYKIGTSGSCPNIT
NGNGFFATMAWAVPKNDKNKT
ATNPLTIEVPYICTEGEDQITVWGFHSDNETQMAKLYGDSKPQKFTSSAN
GVTTHYVSQIGGFPNQTEDGGLPQSGRIVVDYMVQKSGKTGTITYQRGIL
LPQ SEQ ID NO: 17
>A/California/7/2009
GVAPLHLGKCNIAGWILGNPECESLSTASSWSYIVETSSSDNGTCYPGDF
INYEELREQLSSVSSFERFEIFPKTSSWPNEIDSNKGVTAACPHAGAKSF
YKNLIWLVKKGNSYPKLSKSYINDKGKEVLVLWGIHHPSTSADQQSLYQN
ADAYVFVGTSKYSKKFKPEIAVRPKVRDQEGRMNYYWTLVEPGDKITFEA
TGNLLVPRYAFAMERNAGSGIIISD SEQ ID NO: 18
>A/Perth/16/2009_(_K_L)
STGEICDSPHQILDGKNCTLIDALLGDPQCDGFQNKKWDLFVERSKAYSN
CYPYDVPDYASLRSLVASSGTLEFNNESFNWTGVTQNGTSSACIRRSKNS
FFSRLNWLTHLNFKYPALNVTMPNNEQFDKLYIWGVLHPGTDKDQIFLYA
QASGRITVSTKRSQQTVSPNIGSRPRVRNIPSRISIYWTIVKPGDILLIN
STGNLIAPRGYFKIRSGKSSIMRS SEQ ID NO: 19
>A/Victoria/361/2011(M_N_O_)
SIGEICDSPHQILDGENCTLIDALLGDPQCDGFQNKKWDLFVERSKAYSN
CYPYDVPDYASLRSLVASSGTLEFNNESFNWTGVTQNGTSSACIRRSNNS
FFSRLNWLTHLNFKYPALNVTMPNNEQFDKLYIWGVHHPGTDKDQIFLYA
QSSGRITVSTKRSQQAVIPNIGSRPRIRNIPSRISIYWTIVKPGDILLIN
STGNLIAPRGYFKIRSGKSSIMRS SEQ ID NO: 20
>B/Massachusetts/02/2012_(_N_O_)
KTRGKLCPDCLNCTDLDVALGRPMCVGTTPSAKASILHEVRPVTSGCFPI
MHDRTKIRQLANLLRGYENIRLSTQNVIDAEKAPGGPYRLGTSGSCPNAT
SKSGFFATMAWAVPKDNNKNATNPLTVEVPYICAEGEDQITVWGFHSDDK
TQMKNLYGDSNPQKFTSSANGVTTHYVSQIGGFPDQTEDGGLPQSGRIVV
DYMMQKPGKTGTIVYQRGVLLPQK SEQ ID NO: 21
>HIS-tag
HHHHHH SEQ ID NO: 22
>Signal peptide
MRFPSIFTAVLFAASSALAAPVNTTTEDETAQIPAEAVIGYSDLEGDFDV
AVLPFSNSTNNGLLFINTTIASIAAKEEGVSLE

What is claimed is:

1. A polynucleotide comprising:
a nucleotide sequence that encodes three or more isolated, engineered influenza polypeptides;
wherein the three or more isolated, engineered influenza polypeptides (a) comprise a hemagglutinin $HA_1$ domain, and (b) do not comprise a hemagglutinin $HA_2$ domain or a transmembrane domain;
wherein any of the three or more isolated, engineered influenza polypeptides comprises a signal sequence that directs secretion of the polypeptide from a cell;
wherein said cell is a yeast cell.

2. The polynucleotide of claim 1, wherein any of the three or more isolated, engineered influenza polypeptides is from an influenza type A or B.

3. The composition of claim 2, wherein any of the three or more isolated, engineered influenza polypeptides is from an influenza type B.

4. The polynucleotide of claim 2, wherein any of the one three or more isolated, engineered influenza polypeptides is from an influenza type A.

5. The polynucleotide of claim 4, wherein any of the three or more isolated, engineered influenza polypeptides is from an H3N2 subtype.

6. The polynucleotide of claim 1, wherein the $HA_1$ domain of any of the three or more isolated, engineered influenza polypeptides is greater than 40 amino acids in length.

7. The polynucleotide of claim 1 wherein any of the three or more isolated, engineered influenza polypeptides is immunogenic in a human.

8. The polynucleotide of claim 1, wherein the polypeptide sequence of the $HA_1$ domain is A/Victoria/361/2011.

9. The composition of claim 1 wherein any of the three or more isolated, engineered influenza polypeptides comprises an amino acid sequence with at least 90% amino acid sequence identity to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof.

10. The polynucleotide of claim 1, wherein the nucleotide sequence that encodes any of the three or more isolated, engineered influenza polypeptides comprises an amino acid sequence with at least 90% amino acid sequence identity to any of SEQ ID NO: 19 and is codon optimized for expression in yeast.

11. The polynucleotide of claim 1 further comprising:
a pharmaceutically acceptable excipient.

12. The polynucleotide of claim 11, further comprising an immunological adjuvant.

13. A method for immunizing a subject against influenza comprising administering to the subject a composition comprising three or more isolated, engineered influenza polypeptides of claim 1.

* * * * *

SEQUENCE LISTING

<160> NUMBER OF SEQ ID NOS: 31

<210> SEQ ID NO 1
<211> LENGTH: 224
<212> TYPE: PRT
<213> ORGANISM: Influenza A virus

<400> SEQUENCE: 1

Ser Thr Gly Arg Ile Cys Asp Ser Pro His Gln Ile Leu Asp Gly Glu
1               5                   10                  15

Asn Cys Thr Leu Ile Asp Ala Leu Leu Gly Asp Pro His Cys Asp Gly
            20                  25                  30

Phe Gln Asn Lys Glu Trp Asp Leu Phe Val Glu Arg Ser Lys Ala Tyr
        35                  40                  45

Ser Asn Cys Tyr Pro Tyr Asp Val Pro Asp Tyr Ala Ser Leu Arg Ser
    50                  55                  60

-continued

```
Leu Val Ala Ser Ser Gly Thr Leu Glu Phe Asn Asn Glu Ser Phe Asn
65                  70                  75                  80

Trp Thr Gly Val Ala Gln Asn Gly Thr Ser Ser Ala Cys Lys Arg Arg
                85                  90                  95

Ser Ile Lys Ser Phe Phe Ser Arg Leu Asn Trp Leu His Gln Leu Glu
            100                 105                 110

Asn Arg Tyr Pro Ala Leu Asn Val Thr Met Pro Asn Asn Asp Lys Phe
        115                 120                 125

Asp Lys Leu Tyr Ile Trp Gly Val His His Pro Ser Thr Asp Ser Val
    130                 135                 140

Gln Thr Ser Val Tyr Val Gln Ala Ser Gly Arg Val Thr Val Ser Thr
145                 150                 155                 160

Lys Arg Ser Gln Gln Thr Val Ile Pro Asn Ile Gly Ser Arg Pro Trp
                165                 170                 175

Val Arg Gly Val Ser Ser Arg Ile Ser Ile Tyr Trp Thr Ile Val Lys
            180                 185                 190

Pro Gly Asp Ile Leu Leu Ile Asn Ser Thr Gly Asn Leu Ile Ala Pro
        195                 200                 205

Arg Gly Tyr Phe Lys Ile Arg Ser Gly Lys Ser Ser Ile Met Arg Ser
    210                 215                 220

<210> SEQ ID NO 2
<211> LENGTH: 224
<212> TYPE: PRT
<213> ORGANISM: Influenza A virus

<400> SEQUENCE: 2

Gly Ile Ala Pro Leu Gln Leu Gly Asn Cys Ser Val Ala Gly Trp Ile
1               5                   10                  15

Leu Gly Asn Pro Glu Cys Glu Leu Leu Ile Ser Lys Glu Ser Trp Ser
            20                  25                  30

Tyr Ile Val Glu Thr Pro Asn Pro Glu Asn Gly Thr Cys Tyr Pro Gly
        35                  40                  45

Tyr Phe Ala Asp Tyr Glu Glu Leu Arg Glu Gln Leu Ser Ser Val Ser
    50                  55                  60

Ser Phe Glu Arg Phe Glu Ile Phe Pro Lys Glu Ser Ser Trp Pro Asn
65                  70                  75                  80

His Thr Val Thr Gly Val Ser Ala Ser Cys Ser His Asn Gly Lys Ser
                85                  90                  95

Ser Phe Tyr Arg Asn Leu Leu Trp Leu Thr Gly Lys Asn Gly Leu Tyr
            100                 105                 110

Pro Asn Leu Ser Lys Ser Tyr Val Asn Asn Lys Glu Lys Glu Val Leu
        115                 120                 125

Val Leu Trp Gly Val His His Pro Pro Asn Ile Gly Asn Gln Arg Ala
    130                 135                 140

Leu Tyr His Thr Glu Asn Ala Tyr Val Ser Val Val Ser Ser His Tyr
145                 150                 155                 160

Ser Arg Arg Phe Thr Pro Glu Ile Ala Lys Arg Pro Lys Val Arg Asp
                165                 170                 175

Gln Glu Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Trp Tyr Ala
        195                 200                 205

Phe Ala Leu Ser Arg Gly Phe Gly Ser Gly Ile Ile Thr Ser Asn Ala

```
                210                 215                 220
```

\<210\> SEQ ID NO 3
\<211\> LENGTH: 224
\<212\> TYPE: PRT
\<213\> ORGANISM: Influenza B virus

\<400\> SEQUENCE: 3

```
Thr Arg Gly Lys Leu Cys Pro Thr Cys Leu Asn Cys Thr Asp Leu Asp
1               5                   10                  15

Val Ala Leu Gly Arg Pro Met Cys Val Gly Ile Thr Pro Ser Ala Lys
            20                  25                  30

Ala Ser Ile Leu His Glu Ile Lys Pro Val Thr Ser Gly Cys Phe Pro
        35                  40                  45

Ile Met His Asp Arg Thr Lys Ile Arg Gln Leu Pro Asn Leu Leu Arg
    50                  55                  60

Gly Tyr Glu Lys Ile Arg Leu Ser Thr Gln Asn Val Ile Asn Ala Glu
65                  70                  75                  80

Lys Ala Pro Gly Gly Pro Tyr Arg Leu Gly Thr Ser Gly Ser Cys Pro
                85                  90                  95

Asn Ala Thr Ser Lys Ser Gly Phe Phe Ala Thr Met Ala Trp Ala Val
            100                 105                 110

Pro Arg Asp Asn Asn Lys Thr Ala Thr Asn Pro Leu Thr Val Glu Val
        115                 120                 125

Pro His Ile Cys Thr Lys Glu Glu Asp Gln Ile Thr Val Trp Gly Phe
    130                 135                 140

His Ser Asp Asp Lys Thr Gln Met Lys Asn Leu Tyr Gly Asp Ser Asn
145                 150                 155                 160

Pro Gln Lys Phe Thr Ser Ser Ala Asn Gly Ile Thr Thr His Tyr Val
                165                 170                 175

Ser Gln Ile Gly Gly Phe Pro Asp Gln Thr Glu Asp Gly Gly Leu Pro
            180                 185                 190

Gln Ser Gly Arg Ile Val Val Asp Tyr Met Val Gln Lys Pro Gly Lys
        195                 200                 205

Thr Gly Thr Ile Val Tyr Gln Arg Gly Ile Leu Leu Pro Gln Lys Val
    210                 215                 220
```

\<210\> SEQ ID NO 4
\<211\> LENGTH: 224
\<212\> TYPE: PRT
\<213\> ORGANISM: Influenza A virus

\<400\> SEQUENCE: 4

```
Ser Thr Gly Arg Ile Cys Asp Ser Pro His Gln Ile Leu Asp Gly Glu
1               5                   10                  15

Asn Cys Thr Leu Ile Asp Ala Leu Leu Gly Asp Pro His Cys Asp Gly
            20                  25                  30

Phe Gln Asn Lys Glu Trp Asp Leu Phe Val Glu Arg Ser Lys Ala Tyr
        35                  40                  45

Ser Asn Cys Tyr Pro Tyr Asp Val Pro Asp Tyr Ala Ser Leu Arg Ser
    50                  55                  60

Leu Val Ala Ser Ser Gly Thr Leu Glu Phe Asn Asn Glu Ser Phe Asn
65                  70                  75                  80

Trp Thr Gly Val Ala Gln Asn Gly Thr Ser Ser Ala Cys Lys Arg Arg
                85                  90                  95

Ser Asn Lys Ser Phe Phe Ser Arg Leu Asn Trp Leu His Gln Leu Asn
```

```
                100             105             110
Tyr Lys Tyr Pro Ala Leu Asn Val Thr Met Pro Asn Asn Glu Lys Phe
            115                 120                 125

Asp Lys Leu Tyr Ile Trp Gly Val Leu His Pro Ser Thr Asp Ser Asp
        130                 135                 140

Gln Ile Ser Leu Tyr Ala Gln Ala Ser Gly Arg Val Thr Val Ser Thr
145                 150                 155                 160

Lys Arg Ser Gln Gln Thr Val Ile Pro Asn Ile Gly Ser Arg Pro Trp
                165                 170                 175

Val Arg Gly Val Ser Ser Arg Ile Ser Ile Tyr Trp Thr Ile Val Lys
            180                 185                 190

Pro Gly Asp Ile Leu Leu Ile Asn Ser Thr Gly Asn Leu Ile Ala Pro
        195                 200                 205

Arg Gly Tyr Phe Lys Ile Arg Ser Gly Lys Ser Ser Ile Met Arg Ser
    210                 215                 220
```

<210> SEQ ID NO 5
<211> LENGTH: 224
<212> TYPE: PRT
<213> ORGANISM: Influenza B virus

<400> SEQUENCE: 5

```
Lys Thr Arg Gly Lys Leu Cys Pro Lys Cys Leu Asn Cys Thr Asp Leu
1               5                   10                  15

Asp Val Ala Leu Gly Arg Pro Lys Cys Thr Gly Asn Ile Pro Ser Ala
            20                  25                  30

Lys Val Ser Ile Leu His Glu Val Arg Pro Val Thr Ser Gly Cys Phe
        35                  40                  45

Pro Ile Met His Asp Arg Thr Lys Ile Arg Gln Leu Pro Asn Leu Leu
    50                  55                  60

Arg Gly Tyr Glu Arg Ile Arg Leu Ser Asn His Asn Val Ile Asn Ala
65                  70                  75                  80

Glu Lys Ala Pro Gly Gly Pro Tyr Lys Ile Gly Thr Ser Gly Ser Cys
                85                  90                  95

Pro Asn Val Thr Asn Gly Asn Gly Phe Phe Ala Thr Met Ala Trp Ala
            100                 105                 110

Val Pro Lys Asn Glu Asn Asn Lys Thr Ala Thr Asn Ser Leu Thr Ile
        115                 120                 125

Glu Val Pro Tyr Ile Cys Thr Glu Gly Glu Asp Gln Ile Thr Val Trp
    130                 135                 140

Gly Phe His Ser Asp Ser Glu Thr Gln Met Ala Lys Leu Tyr Gly Asp
145                 150                 155                 160

Ser Lys Pro Gln Lys Phe Thr Ser Ser Ala Asn Gly Val Thr Thr His
                165                 170                 175

Tyr Val Ser Gln Ile Gly Gly Phe Pro Asn Gln Thr Glu Asp Gly Gly
            180                 185                 190

Leu Pro Gln Ser Gly Arg Ile Val Val Asp Tyr Met Val Gln Lys Ser
        195                 200                 205

Gly Lys Thr Gly Thr Ile Thr Tyr Gln Arg Gly Ile Leu Leu Pro Gln
    210                 215                 220
```

<210> SEQ ID NO 6
<211> LENGTH: 224
<212> TYPE: PRT
<213> ORGANISM: Influenza A virus

```
<400> SEQUENCE: 6

Ser Thr Gly Gly Ile Cys Asp Ser Pro His Gln Ile Leu Asp Gly Glu
1               5                   10                  15

Asn Cys Thr Leu Ile Asp Ala Leu Leu Gly Asp Pro Gln Cys Asp Gly
            20                  25                  30

Phe Gln Asn Lys Lys Trp Asp Leu Phe Val Glu Arg Ser Lys Ala Tyr
        35                  40                  45

Ser Asn Cys Tyr Pro Tyr Asp Val Pro Asp Tyr Ala Ser Leu Arg Ser
50                  55                  60

Leu Val Ala Ser Ser Gly Thr Leu Glu Phe Asn Asn Glu Ser Phe Asn
65                  70                  75                  80

Trp Ala Gly Val Thr Gln Asn Gly Thr Ser Ala Cys Lys Arg Arg
                85                  90                  95

Ser Asn Lys Ser Phe Phe Ser Arg Leu Asn Trp Leu Thr His Leu Lys
            100                 105                 110

Tyr Lys Tyr Pro Ala Leu Asn Val Thr Met Pro Asn Asn Glu Lys Phe
        115                 120                 125

Asp Lys Leu Tyr Ile Trp Gly Val His His Pro Val Thr Asp Ser Glu
130                 135                 140

Gln Ile Ser Leu Tyr Ala Gln Ala Ser Gly Arg Ile Thr Val Ser Thr
145                 150                 155                 160

Lys Arg Ser Gln Gln Thr Val Ile Pro Asn Ile Gly Tyr Arg Pro Arg
                165                 170                 175

Val Arg Asp Ile Ser Ser Arg Ile Ser Ile Tyr Trp Thr Ile Val Lys
            180                 185                 190

Pro Gly Asp Ile Leu Leu Ile Asn Ser Thr Gly Asn Leu Ile Ala Pro
        195                 200                 205

Arg Gly Tyr Phe Lys Ile Arg Ser Gly Lys Ser Ser Ile Met Arg Ser
210                 215                 220

<210> SEQ ID NO 7
<211> LENGTH: 224
<212> TYPE: PRT
<213> ORGANISM: Influenza B virus

<400> SEQUENCE: 7

Thr Asp Leu Asp Val Ala Leu Gly Arg Pro Met Cys Val Gly Thr Thr
1               5                   10                  15

Pro Ser Ala Lys Ala Ser Ile Leu His Glu Val Arg Pro Val Thr Ser
            20                  25                  30

Gly Cys Phe Pro Ile Met His Asp Arg Thr Lys Ile Arg Gln Leu Pro
        35                  40                  45

Asn Leu Leu Arg Gly Tyr Glu Asn Ile Arg Leu Ser Thr Gln Asn Val
50                  55                  60

Ile Asp Ala Glu Lys Ala Leu Gly Gly Pro Tyr Arg Leu Gly Thr Ser
65                  70                  75                  80

Gly Ser Cys Pro Asn Ala Thr Ser Lys Ser Gly Phe Phe Ala Thr Met
                85                  90                  95

Ala Trp Ala Val Pro Lys Asp Asn Asn Lys Asn Ala Thr Asn Pro Leu
            100                 105                 110

Thr Val Glu Val Pro Tyr Ile Cys Thr Glu Gly Glu Asp Gln Ile Thr
        115                 120                 125

Val Trp Gly Phe His Ser Asp Asp Lys Thr Gln Met Lys Asn Leu Tyr
130                 135                 140
```

Gly Asp Ser Asn Pro Gln Lys Phe Thr Ser Ala Asn Gly Val Thr
145                 150                 155                 160

Thr His Tyr Val Ser Gln Ile Gly Gly Phe Pro Asp Gln Thr Glu Asp
                165                 170                 175

Gly Gly Leu Pro Gln Ser Gly Arg Ile Val Val Asp Tyr Met Val Gln
            180                 185                 190

Lys Pro Gly Lys Thr Gly Thr Ile Val Tyr Gln Arg Gly Val Leu Leu
        195                 200                 205

Pro Gln Lys Val Trp Cys Ala Ser Gly Arg Ser Lys Val Ile Lys Gly
    210                 215                 220

<210> SEQ ID NO 8
<211> LENGTH: 224
<212> TYPE: PRT
<213> ORGANISM: Influenza A virus

<400> SEQUENCE: 8

Ser Thr Gly Gly Ile Cys Asp Ser Pro His Gln Ile Leu Asp Gly Glu
1               5                   10                  15

Asn Cys Thr Leu Ile Asp Ala Leu Leu Gly Asp Pro Gln Cys Asp Gly
            20                  25                  30

Phe Gln Asn Lys Lys Trp Asp Leu Phe Val Glu Arg Ser Lys Ala Tyr
        35                  40                  45

Ser Asn Cys Tyr Pro Tyr Asp Val Pro Asp Tyr Ala Ser Leu Arg Ser
    50                  55                  60

Leu Val Ala Ser Ser Gly Thr Leu Glu Phe Asn Asp Glu Ser Phe Asn
65                  70                  75                  80

Trp Thr Gly Val Thr Gln Asn Gly Thr Ser Ser Cys Lys Arg Arg
                85                  90                  95

Ser Asn Asn Ser Phe Phe Ser Arg Leu Asn Trp Leu Thr His Leu Lys
            100                 105                 110

Phe Lys Tyr Pro Ala Leu Asn Val Thr Met Pro Asn Asn Glu Lys Phe
        115                 120                 125

Asp Lys Leu Tyr Ile Trp Gly Val His His Pro Val Thr Asp Asn Asp
    130                 135                 140

Gln Ile Phe Leu Tyr Ala Gln Ala Ser Gly Arg Ile Thr Val Ser Thr
145                 150                 155                 160

Lys Arg Ser Gln Gln Thr Val Ile Pro Asn Ile Gly Ser Arg Pro Arg
                165                 170                 175

Ile Arg Asn Ile Pro Ser Arg Ile Ser Ile Tyr Trp Thr Ile Val Lys
            180                 185                 190

Pro Gly Asp Ile Leu Leu Ile Asn Ser Thr Gly Asn Leu Ile Ala Pro
        195                 200                 205

Arg Gly Tyr Phe Lys Ile Arg Ser Gly Lys Ser Ser Ile Met Arg Ser
    210                 215                 220

<210> SEQ ID NO 9
<211> LENGTH: 224
<212> TYPE: PRT
<213> ORGANISM: Influenza B virus
<220> FEATURE:
<221> NAME/KEY: MOD_RES
<222> LOCATION: (152)..(152)
<223> OTHER INFORMATION: Any amino acid

<400> SEQUENCE: 9

Glu Thr Arg Gly Lys Leu Cys Pro Lys Cys Leu Asn Cys Thr Asp Leu
1 5 10 15

```
Asp Val Ala Leu Gly Arg Pro Lys Cys Thr Gly Asn Ile Pro Ser Ala
            20                  25                  30

Arg Val Ser Ile Leu His Glu Val Arg Pro Val Thr Ser Gly Cys Phe
        35                  40                  45

Pro Ile Met His Asp Arg Thr Lys Ile Arg Gln Leu Pro Asn Leu Leu
 50                  55                  60

Arg Gly Tyr Glu His Ile Arg Leu Ser Thr His Asn Val Ile Asn Ala
 65                  70                  75                  80

Glu Asn Ala Pro Gly Gly Pro Tyr Lys Ile Gly Thr Ser Gly Ser Cys
                 85                  90                  95

Pro Asn Val Thr Asn Gly Asn Gly Phe Phe Ala Thr Met Ala Trp Ala
            100                 105                 110

Val Pro Lys Asn Asp Asn Asn Lys Thr Ala Thr Asn Ser Leu Thr Ile
        115                 120                 125

Glu Val Pro Tyr Ile Cys Thr Glu Gly Glu Asp Gln Ile Thr Val Trp
130                 135                 140

Gly Phe His Ser Asp Asn Glu Xaa Gln Met Ala Lys Leu Tyr Gly Asp
145                 150                 155                 160

Ser Lys Pro Gln Lys Phe Thr Ser Ser Ala Asn Gly Val Thr Thr His
                165                 170                 175

Tyr Val Ser Gln Ile Gly Gly Phe Pro Asn Gln Thr Glu Asp Gly Gly
            180                 185                 190

Leu Pro Gln Ser Gly Arg Ile Val Val Asp Tyr Met Val Gln Lys Ser
        195                 200                 205

Gly Lys Thr Gly Thr Ile Thr Tyr Gln Arg Gly Ile Leu Leu Pro Gln
210                 215                 220

<210> SEQ ID NO 10
<211> LENGTH: 224
<212> TYPE: PRT
<213> ORGANISM: Influenza A virus

<400> SEQUENCE: 10

Ser Thr Gly Gly Ile Cys Asp Ser Pro His Gln Ile Leu Asp Gly Glu
1               5                   10                  15

Asn Cys Thr Leu Ile Asp Ala Leu Leu Gly Asp Pro Gln Cys Asp Gly
            20                  25                  30

Phe Gln Asn Lys Lys Trp Asp Leu Phe Val Glu Arg Ser Lys Ala Tyr
        35                  40                  45

Ser Asn Cys Tyr Pro Tyr Asp Val Pro Asp Tyr Ala Ser Leu Arg Ser
 50                  55                  60

Leu Val Ala Ser Ser Gly Thr Leu Glu Phe Asn Asn Glu Ser Phe Asn
65                   70                  75                  80

Trp Thr Gly Val Thr Gln Asn Gly Thr Ser Ser Ala Cys Lys Arg Arg
                85                  90                  95

Ser Asn Asn Ser Phe Phe Ser Arg Leu Asn Trp Leu Thr Gln Leu Lys
            100                 105                 110

Phe Lys Tyr Pro Ala Leu Lys Val Thr Met Pro Asn Asn Glu Lys Phe
        115                 120                 125

Asp Lys Leu Tyr Ile Trp Gly Val His His Pro Val Thr Asp Asn Asp
130                 135                 140

Gln Ile Phe Leu Tyr Ala Gln Ala Ser Gly Arg Ile Thr Val Ser Thr
145                 150                 155                 160

Lys Arg Ser Gln Gln Thr Val Ile Pro Asn Ile Gly Ser Arg Pro Arg
```

```
                    165                 170                 175
Val Arg Asn Ile Pro Ser Arg Ile Ser Ile Tyr Trp Thr Ile Val Lys
                180                 185                 190

Pro Gly Asp Ile Leu Leu Ile Asn Ser Thr Gly Asn Leu Ile Ala Pro
            195                 200                 205

Arg Gly Tyr Phe Lys Ile Arg Ser Gly Lys Ser Ser Ile Met Arg Ser
        210                 215                 220

<210> SEQ ID NO 11
<211> LENGTH: 224
<212> TYPE: PRT
<213> ORGANISM: Influenza B virus

<400> SEQUENCE: 11

Leu Asp Val Ala Leu Gly Arg Pro Lys Cys Thr Gly Asn Ile Pro Ser
1               5                   10                  15

Ala Glu Val Ser Ile Leu His Glu Val Arg Pro Val Thr Ser Gly Cys
            20                  25                  30

Phe Pro Ile Met His Asp Arg Thr Lys Ile Arg Gln Leu Pro Asn Leu
        35                  40                  45

Leu Arg Gly Tyr Glu His Ile Arg Leu Ser Thr His Asn Val Ile Asn
    50                  55                  60

Ala Glu Lys Ala Pro Gly Gly Pro Tyr Lys Ile Gly Thr Ser Gly Ser
65                  70                  75                  80

Cys Pro Asn Val Thr Asn Gly Asn Gly Phe Phe Ala Thr Met Ala Trp
                85                  90                  95

Ala Val Pro Lys Asn Asp Asn Asn Lys Thr Ala Thr Asn Ser Leu Thr
            100                 105                 110

Ile Glu Val Pro Tyr Ile Cys Thr Glu Gly Glu Asp Gln Ile Thr Ile
        115                 120                 125

Trp Gly Phe His Ser Asp Ser Glu Thr Gln Met Ala Lys Leu Tyr Gly
    130                 135                 140

Asp Ser Lys Pro Gln Lys Phe Thr Ser Ser Ala Asn Gly Val Thr Thr
145                 150                 155                 160

His Tyr Val Ser Gln Ile Gly Gly Phe Pro Asn Gln Thr Glu Asp Gly
                165                 170                 175

Gly Leu Pro Gln Ser Gly Arg Ile Val Val Asp Tyr Met Val Gln Lys
            180                 185                 190

Ser Gly Lys Thr Gly Thr Ile Thr Tyr Gln Arg Gly Ile Leu Leu Pro
        195                 200                 205

Gln Lys Val Trp Cys Ala Ser Gly Arg Ser Lys Val Ile Lys Gly Ser
    210                 215                 220

<210> SEQ ID NO 12
<211> LENGTH: 224
<212> TYPE: PRT
<213> ORGANISM: Influenza A virus

<400> SEQUENCE: 12

Gly Ile Ala Pro Leu Gln Leu Gly Asn Cys Ser Val Ala Gly Trp Ile
1               5                   10                  15

Leu Gly Asn Pro Glu Cys Glu Leu Leu Ile Ser Arg Glu Ser Trp Ser
            20                  25                  30

Tyr Ile Val Glu Lys Pro Asn Pro Glu Asn Gly Thr Cys Tyr Pro Gly
        35                  40                  45

His Phe Ala Asp Tyr Glu Glu Leu Arg Glu Gln Leu Ser Ser Val Ser
```

```
                    50                  55                  60
Ser Phe Glu Arg Phe Glu Ile Phe Pro Lys Glu Ser Ser Trp Pro Asn
 65                  70                  75                  80

His Thr Thr Thr Gly Val Ser Ala Ser Cys Ser His Asn Gly Glu Ser
                     85                  90                  95

Ser Phe Tyr Lys Asn Leu Leu Trp Leu Thr Gly Lys Asn Gly Leu Tyr
                100                 105                 110

Pro Asn Leu Ser Lys Ser Tyr Ala Asn Asn Lys Glu Lys Glu Val Leu
            115                 120                 125

Val Leu Trp Gly Val His His Pro Pro Asn Ile Gly Asp Gln Arg Ala
130                 135                 140

Leu Tyr His Thr Glu Asn Ala Tyr Val Ser Val Val Ser Ser His Tyr
145                 150                 155                 160

Ser Arg Lys Phe Thr Pro Glu Ile Ala Lys Arg Pro Lys Val Arg Asp
                165                 170                 175

Arg Glu Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Arg Tyr Ala
        195                 200                 205

Phe Ala Leu Ser Arg Gly Phe Gly Ser Gly Ile Ile Asn Ser Asn Ala
210                 215                 220

<210> SEQ ID NO 13
<211> LENGTH: 224
<212> TYPE: PRT
<213> ORGANISM: Influenza A virus

<400> SEQUENCE: 13

Gly Ile Ala Pro Leu Gln Leu Gly Asn Cys Ser Val Ala Gly Trp Ile
  1               5                  10                  15

Leu Gly Asn Pro Glu Cys Glu Leu Leu Ile Ser Lys Glu Ser Trp Ser
                 20                  25                  30

Tyr Ile Val Glu Lys Pro Asn Pro Glu Asn Gly Thr Cys Tyr Pro Gly
             35                  40                  45

His Phe Ala Asp Tyr Glu Glu Leu Arg Glu Gln Leu Ser Ser Val Ser
 50                  55                  60

Ser Phe Glu Arg Phe Glu Ile Phe Pro Lys Glu Ser Ser Trp Pro Asn
 65                  70                  75                  80

His Thr Val Thr Gly Val Ser Ala Ser Cys Ser His Asn Gly Glu Ser
                     85                  90                  95

Ser Phe Tyr Arg Asn Leu Leu Trp Leu Thr Gly Lys Asn Gly Leu Tyr
                100                 105                 110

Pro Asn Leu Ser Lys Ser Tyr Ala Asn Asn Lys Glu Lys Glu Val Leu
            115                 120                 125

Val Leu Trp Gly Val His His Pro Pro Asn Ile Gly Asn Gln Lys Ala
130                 135                 140

Leu Tyr His Thr Glu Asn Ala Tyr Val Ser Val Val Ser Ser His Tyr
145                 150                 155                 160

Ser Arg Lys Phe Thr Pro Glu Ile Ala Lys Arg Pro Lys Val Arg Asp
                165                 170                 175

Gln Glu Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Arg Tyr Ala
        195                 200                 205
```

```
Phe Ala Leu Ser Arg Gly Phe Gly Ser Gly Ile Ile Asn Ser Asn Ala
    210                 215                 220
```

<210> SEQ ID NO 14
<211> LENGTH: 224
<212> TYPE: PRT
<213> ORGANISM: Influenza A virus

<400> SEQUENCE: 14

```
Ser Thr Gly Glu Ile Cys Asp Ser Pro His Gln Ile Leu Asp Gly Glu
1               5                   10                  15

Asn Cys Thr Leu Ile Asp Ala Leu Leu Gly Asp Pro Gln Cys Asp Gly
            20                  25                  30

Phe Gln Asn Lys Lys Trp Asp Leu Phe Val Glu Arg Ser Lys Ala Tyr
        35                  40                  45

Ser Asn Cys Tyr Pro Tyr Asp Val Pro Asp Tyr Ala Ser Leu Arg Ser
    50                  55                  60

Leu Val Ala Ser Ser Gly Thr Leu Glu Phe Asn Asn Glu Ser Phe Asn
65                  70                  75                  80

Trp Thr Gly Val Thr Gln Asn Gly Thr Ser Ser Ala Cys Ile Arg Arg
                85                  90                  95

Ser Asn Asn Ser Phe Phe Ser Arg Leu Asn Trp Leu Thr His Leu Lys
            100                 105                 110

Phe Lys Tyr Pro Ala Leu Asn Val Thr Met Pro Asn Asn Glu Lys Phe
        115                 120                 125

Asp Lys Leu Tyr Ile Trp Gly Val His His Pro Gly Thr Asp Asn Asp
    130                 135                 140

Gln Ile Phe Leu Tyr Ala Gln Ala Ser Gly Arg Ile Thr Val Ser Thr
145                 150                 155                 160

Lys Arg Ser Gln Gln Thr Val Ile Pro Asn Ile Gly Ser Arg Pro Arg
                165                 170                 175

Val Arg Asn Ile Pro Ser Arg Ile Ser Ile Tyr Trp Thr Ile Val Lys
            180                 185                 190

Pro Gly Asp Ile Leu Leu Ile Asn Ser Thr Gly Asn Leu Ile Ala Pro
        195                 200                 205

Arg Gly Tyr Phe Lys Ile Arg Ser Gly Lys Ser Ser Ile Met Arg Ser
    210                 215                 220
```

<210> SEQ ID NO 15
<211> LENGTH: 224
<212> TYPE: PRT
<213> ORGANISM: Influenza B virus

<400> SEQUENCE: 15

```

```
Pro Asn Ala Thr Ser Lys Ser Gly Phe Phe Ala Thr Met Ala Trp Ala
            100                 105                 110

Val Pro Lys Asp Asn Asn Lys Asn Ala Thr Asn Pro Leu Thr Val Glu
        115                 120                 125

Val Pro Tyr Ile Cys Thr Glu Gly Glu Asp Gln Ile Thr Val Trp Gly
        130                 135                 140

Phe His Ser Asp Asp Lys Thr Gln Met Lys Asn Leu Tyr Gly Asp Ser
145                 150                 155                 160

Asn Pro Gln Lys Phe Thr Ser Ser Ala Asn Gly Val Thr Thr His Tyr
                165                 170                 175

Val Ser Gln Ile Gly Ser Phe Pro Asp Gln Thr Glu Asp Gly Gly Leu
            180                 185                 190

Pro Gln Ser Gly Arg Ile Val Val Asp Tyr Met Met Gln Lys Pro Gly
        195                 200                 205

Lys Thr Gly Thr Ile Val Tyr Gln Arg Gly Val Leu Leu Pro Gln Lys
        210                 215                 220
```

<210> SEQ ID NO 16
<211> LENGTH: 224
<212> TYPE: PRT
<213> ORGANISM: Influenza B virus

<400> SEQUENCE: 16

```
Glu Thr Arg Gly Lys Leu Cys Pro Lys Cys Leu Asn Cys Thr Asp Leu
1               5                   10                  15

Asp Val Ala Leu Gly Arg Pro Lys Cys Thr Gly Lys Ile Pro Ser Ala
            20                  25                  30

Arg Val Ser Ile Leu His Glu Val Arg Pro Val Thr Ser Gly Cys Phe
        35                  40                  45

Pro Ile Met His Asp Arg Thr Lys Ile Arg Gln Leu Pro Asn Leu Leu
    50                  55                  60

Arg Gly Tyr Glu His Ile Arg Leu Ser Thr His Asn Val Ile Asn Ala
65                  70                  75                  80

Glu Asn Ala Pro Gly Gly Pro Tyr Lys Ile Gly Thr Ser Gly Ser Cys
                85                  90                  95

Pro Asn Ile Thr Asn Gly Asn Gly Phe Phe Ala Thr Met Ala Trp Ala
            100                 105                 110

Val Pro Lys Asn Asp Lys Asn Lys Thr Ala Thr Asn Pro Leu Thr Ile
        115                 120                 125

Glu Val Pro Tyr Ile Cys Thr Glu Gly Glu Asp Gln Ile Thr Val Trp
        130                 135                 140

Gly Phe His Ser Asp Asn Glu Thr Gln Met Ala Lys Leu Tyr Gly Asp
145                 150                 155                 160

Ser Lys Pro Gln Lys Phe Thr Ser Ser Ala Asn Gly Val Thr Thr His
                165                 170                 175

Tyr Val Ser Gln Ile Gly Gly Phe Pro Asn Gln Thr Glu Asp Gly Gly
            180                 185                 190

Leu Pro Gln Ser Gly Arg Ile Val Val Asp Tyr Met Val Gln Lys Ser
        195                 200                 205

Gly Lys Thr Gly Thr Ile Thr Tyr Gln Arg Gly Ile Leu Leu Pro Gln
        210                 215                 220
```

<210> SEQ ID NO 17
<211> LENGTH: 224
<212> TYPE: PRT
<213> ORGANISM: Influenza A virus

<400> SEQUENCE: 17

```
Gly Val Ala Pro Leu His Leu Gly Lys Cys Asn Ile Ala Gly Trp Ile
1               5                   10                  15
Leu Gly Asn Pro Glu Cys Glu Ser Leu Ser Thr Ala Ser Ser Trp Ser
            20                  25                  30
Tyr Ile Val Glu Thr Ser Ser Asp Asn Gly Thr Cys Tyr Pro Gly
        35                  40                  45
Asp Phe Ile Asn Tyr Glu Glu Leu Arg Glu Gln Leu Ser Ser Val Ser
    50                  55                  60
Ser Phe Glu Arg Phe Glu Ile Phe Pro Lys Thr Ser Ser Trp Pro Asn
65                  70                  75                  80
His Asp Ser Asn Lys Gly Val Thr Ala Ala Cys Pro His Ala Gly Ala
                85                  90                  95
Lys Ser Phe Tyr Lys Asn Leu Ile Trp Leu Val Lys Lys Gly Asn Ser
            100                 105                 110
Tyr Pro Lys Leu Ser Lys Ser Tyr Ile Asn Asp Lys Gly Lys Glu Val
        115                 120                 125
Leu Val Leu Trp Gly Ile His His Pro Ser Thr Ser Ala Asp Gln Gln
130                 135                 140
Ser Leu Tyr Gln Asn Ala Asp Ala Tyr Val Phe Val Gly Thr Ser Lys
145                 150                 155                 160
Tyr Ser Lys Lys Phe Lys Pro Glu Ile Ala Val Arg Pro Lys Val Arg
                165                 170                 175
Asp Gln Glu Gly Arg Met Asn Tyr Tyr Trp Thr Leu Val Glu Pro Gly
            180                 185                 190
Asp Lys Ile Thr Phe Glu Ala Thr Gly Asn Leu Leu Val Pro Arg Tyr
        195                 200                 205
Ala Phe Ala Met Glu Arg Asn Ala Gly Ser Gly Ile Ile Ile Ser Asp
    210                 215                 220

<210> SEQ ID NO 18
<211> LENGTH: 224
<212> TYPE: PRT
<213> ORGANISM: Influenza A virus

<400> SEQUENCE: 18

Ser Thr Gly Glu Ile Cys Asp Ser Pro His Gln Ile Leu Asp Gly Lys
1               5                   10                  15
Asn Cys Thr Leu Ile Asp Ala Leu Leu Gly Asp Pro Gln Cys Asp Gly
            20                  25                  30
Phe Gln Asn Lys Lys Trp Asp Leu Phe Val Glu Arg Ser Lys Ala Tyr
        35                  40                  45
Ser Asn Cys Tyr Pro Tyr Asp Val Pro Asp Tyr Ala Ser Leu Arg Ser
    50                  55                  60
Leu Val Ala Ser Ser Gly Thr Leu Glu Phe Asn Asn Glu Ser Phe Asn
65                  70                  75                  80
Trp Thr Gly Val Thr Gln Asn Gly Thr Ser Ser Ala Cys Ile Arg Arg
                85                  90                  95
Ser Lys Asn Ser Phe Phe Ser Arg Leu Asn Trp Leu Thr His Leu Asn
            100                 105                 110
Phe Lys Tyr Pro Ala Leu Asn Val Thr Met Pro Asn Asn Glu Gln Phe
        115                 120                 125
Asp Lys Leu Tyr Ile Trp Gly Val Leu His Pro Gly Thr Asp Lys Asp
130                 135                 140
```

-continued

Gln Ile Phe Leu Tyr Ala Gln Ala Ser Gly Arg Ile Thr Val Ser Thr
145                 150                 155                 160

Lys Arg Ser Gln Gln Thr Val Ser Pro Asn Ile Gly Ser Arg Pro Arg
                165                 170                 175

Val Arg Asn Ile Pro Ser Arg Ile Ser Ile Tyr Trp Thr Ile Val Lys
            180                 185                 190

Pro Gly Asp Ile Leu Leu Ile Asn Ser Thr Gly Asn Leu Ile Ala Pro
        195                 200                 205

Arg Gly Tyr Phe Lys Ile Arg Ser Gly Lys Ser Ser Ile Met Arg Ser
    210                 215                 220

<210> SEQ ID NO 19
<211> LENGTH: 224
<212> TYPE: PRT
<213> ORGANISM: Influenza A virus

<400> SEQUENCE: 19

Ser Ile Gly Glu Ile Cys Asp Ser Pro His Gln Ile Leu Asp Gly Glu
1               5                   10                  15

Asn Cys Thr Leu Ile Asp Ala Leu Leu Gly Asp Pro Gln Cys Asp Gly
            20                  25                  30

Phe Gln Asn Lys Lys Trp Asp Leu Phe Val Glu Arg Ser Lys Ala Tyr
        35                  40                  45

Ser Asn Cys Tyr Pro Tyr Asp Val Pro Asp Tyr Ala Ser Leu Arg Ser
    50                  55                  60

Leu Val Ala Ser Ser Gly Thr Leu Glu Phe Asn Asn Glu Ser Phe Asn
65                  70                  75                  80

Trp Thr Gly Val Thr Gln Asn Gly Thr Ser Ser Ala Cys Ile Arg Arg
                85                  90                  95

Ser Asn Asn Ser Phe Phe Ser Arg Leu Asn Trp Leu Thr His Leu Asn
            100                 105                 110

Phe Lys Tyr Pro Ala Leu Asn Val Thr Met Pro Asn Asn Glu Gln Phe
        115                 120                 125

Asp Lys Leu Tyr Ile Trp Gly Val His His Pro Gly Thr Asp Lys Asp
    130                 135                 140

Gln Ile Phe Leu Tyr Ala Gln Ser Ser Gly Arg Ile Thr Val Ser Thr
145                 150                 155                 160

Lys Arg Ser Gln Gln Ala Val Ile Pro Asn Ile Gly Ser Arg Pro Arg
                165                 170                 175

Ile Arg Asn Ile Pro Ser Arg Ile Ser Ile Tyr Trp Thr Ile Val Lys
            180                 185                 190

Pro Gly Asp Ile Leu Leu Ile Asn Ser Thr Gly Asn Leu Ile Ala Pro
        195                 200                 205

Arg Gly Tyr Phe Lys Ile Arg Ser Gly Lys Ser Ser Ile Met Arg Ser
    210                 215                 220

<210> SEQ ID NO 20
<211> LENGTH: 224
<212> TYPE: PRT
<213> ORGANISM: Influenza B virus

<400> SEQUENCE: 20

Lys Thr Arg Gly Lys Leu Cys Pro Asp Cys Leu Asn Cys Thr Asp Leu
1               5                   10                  15

Asp Val Ala Leu Gly Arg Pro Met Cys Val Gly Thr Thr Pro Ser Ala
            20                  25                  30

Lys Ala Ser Ile Leu His Glu Val Arg Pro Val Thr Ser Gly Cys Phe
            35                  40                  45

Pro Ile Met His Asp Arg Thr Lys Ile Arg Gln Leu Ala Asn Leu Leu
     50                  55                  60

Arg Gly Tyr Glu Asn Ile Arg Leu Ser Thr Gln Asn Val Ile Asp Ala
 65                  70                  75                  80

Glu Lys Ala Pro Gly Gly Pro Tyr Arg Leu Gly Thr Ser Gly Ser Cys
                 85                  90                  95

Pro Asn Ala Thr Ser Lys Ser Gly Phe Phe Ala Thr Met Ala Trp Ala
            100                 105                 110

Val Pro Lys Asp Asn Asn Lys Asn Ala Thr Asn Pro Leu Thr Val Glu
        115                 120                 125

Val Pro Tyr Ile Cys Ala Glu Gly Glu Asp Gln Ile Thr Val Trp Gly
    130                 135                 140

Phe His Ser Asp Asp Lys Thr Gln Met Lys Asn Leu Tyr Gly Asp Ser
145                 150                 155                 160

Asn Pro Gln Lys Phe Thr Ser Ser Ala Asn Gly Val Thr Thr His Tyr
                165                 170                 175

Val Ser Gln Ile Gly Gly Phe Pro Asp Gln Thr Glu Asp Gly Gly Leu
            180                 185                 190

Pro Gln Ser Gly Arg Ile Val Val Asp Tyr Met Met Gln Lys Pro Gly
        195                 200                 205

Lys Thr Gly Thr Ile Val Tyr Gln Arg Gly Val Leu Leu Pro Gln Lys
    210                 215                 220

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu

```
<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 23

His His His His His His His His His His
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Gln Lys Leu Ile Ser Glu Glu Asp Leu
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Tyr Lys Asp Asp Asp Asp Lys
1               5

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Lys Pro Ile Pro Asn Pro Leu Leu Gly Leu Asp Ser Thr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Thr Asp Ile Glu Met Asn Arg Leu Gly Lys
1               5                   10

<210> SEQ ID NO 28
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 28

Asp Asp Asp Asp Lys
1               5

<210> SEQ ID NO 29
<211> LENGTH: 9
<212> TYPE: PRT
<213> ORGANISM: Human rhinovirus
<220> FEATURE:
<221> NAME/KEY: MOD_RES
<222> LOCATION: (9)..(9)
<223> OTHER INFORMATION: Any amino acid

<400> SEQUENCE: 29

Leu Glu Val Leu Phe Gln Gly Pro Xaa
1               5

<210> SEQ ID NO 30
<211> LENGTH: 8
<212> TYPE: PRT
<213> ORGANISM: Tobacco etch virus
<220> FEATURE:
<221> NAME/KEY: MOD_RES
<222> LOCATION: (8)..(8)
<223> OTHER INFORMATION: Any amino acid

<400> SEQUENCE: 30

Glu Asn Leu Tyr Phe Gln Gly Xaa
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid except Pro

<400> SEQUENCE: 31

Asp Asp Asp Asp Lys Xaa
1               5
```